(12) United States Patent
Kalinichenko et al.

(10) Patent No.: US 9,682,072 B2
(45) Date of Patent: Jun. 20, 2017

(54) COMPOSITIONS AND METHODS FOR TREATMENT OF LUNG DYSFUNCTION

(71) Applicant: Children's Hospital Medical Center, Cincinnati, OH (US)

(72) Inventors: Vladimir Kalinichenko, Cincinnati, OH (US); Tatiana Kalin, Cincinnati, OH (US); Jeffrey A. Whitsett, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 15/289,589

(22) Filed: Oct. 10, 2016

(65) Prior Publication Data
US 2017/0105982 A1    Apr. 20, 2017

Related U.S. Application Data

(60) Provisional application No. 62/241,412, filed on Oct. 14, 2015.

(51) Int. Cl.
*A61K 31/4436* (2006.01)
*A61K 9/00* (2006.01)

(52) U.S. Cl.
CPC ........ *A61K 31/4436* (2013.01); *A61K 9/0019* (2013.01); *A61K 9/0073* (2013.01)

(58) Field of Classification Search
CPC .......................... A61K 31/4436; A61K 9/0019
See application file for complete search history.

(56) References Cited

U.S. PATENT DOCUMENTS 8,642,660 B2 *    2/2014   Goldfarb .............. A61K 31/122
                                                                514/18.9

\* cited by examiner

*Primary Examiner* — Golam M M Shameem
(74) *Attorney, Agent, or Firm* — Frost Brown Todd LLC

(57) ABSTRACT

Described are compositions and methods for the treatment, prevention, or amelioration of a symptom of an airway disorder. In certain aspects, the airway disorder may be one characterized by one or more conditions, such as goblet cell metaplasia, lung tissue inflammation, increased airway hyperresponsiveness, mucus hyperplasia, decreased airway resistance, and increased production of pro-inflammatory cytokines. The compositions and methods may be useful for the treatment of an airway disorder such as asthma, chronic obstructive pulmonary disease (COPD), cystic fibrosis (CF), allergic disorders, pulmonary inflammatory diseases, pulmonary fibrosis, and/or interstitial lung diseases.

6 Claims, 24 Drawing Sheets

Cell Counts (BALF)

Histology Scores (Lung Tissue)

Total Lung (qRT-PCR)

Total Lung (qRT-PCR)

BALF (ELISA)

Human Airway Epithelial Cells

A549 Cells

Nuclear/Cytoplasmic GFP

FIG 8E (suppl)

Cells in BALF

IL-13 + RCM-1 Treatment Protocol

COMPOSITIONS AND METHODS FOR TREATMENT OF LUNG DYSFUNCTION

CROSS REFERENCE TO RELATED APPLICATIONS

This application claims the benefit of and priority to U.S. Provisional Application Ser. No. 62/241,412, filed Oct. 14, 2015, in its entirety and for all purposes.

BACKGROUND

Asthma is a common chronic pulmonary disorder, associated with mucus hyperproduction, persistent pulmonary inflammation, airway hyperresponsiveness, and tissue remodeling (1, 2). Similarly, other lung related disease states such as cystic fibrosis and chronic obstructive pulmonary disease are characterized by one or more of these symptoms, which contribute to patient morbidity and mortality, and for which current therapies are not always sufficient for successful treatment.

While there are many mucolytics and agents targeting airway fluid production, there is a lack of therapeutic agents that directly target transcriptional networks critical for differentiation of mucin-producing goblet cells. Traditionally, transcription factors have been considered "undrugable" targets, such that active agents directed to the modulation of transcription factors to treat disease have not been considered feasible and have not been actively pursued.

The instant disclosure addresses one or more of the aforementioned problems in the art.

BRIEF SUMMARY

Disclosed herein are compositions and methods for the treatment, prevention, or amelioration of a symptom of an airway disorder. In certain aspects, the airway disorder may be characterized by one or more conditions, such as goblet cell metaplasia, lung tissue inflammation, increased airway hyperresponsiveness, mucus hyperplasia, decreased airway resistance, and increased production of pro-inflammatory cytokines. The compositions and methods may be useful for the treatment of an airway disorder such as asthma, chronic obstructive pulmonary disease (COPD), cystic fibrosis (CF), allergic disorders, pulmonary inflammatory diseases, pulmonary fibrosis, and/or interstitial lung diseases.

BRIEF DESCRIPTION OF THE DRAWINGS

FIG. 1A, Schematic drawing of the high-throughput screen. U2OS C3 cells containing Dox-inducible GFP-FOXM1 construct were plated 2000 cells per well. Sixteen hours later, Dox was added to the cell culture. After 24-hr, 50,000 small molecule compounds were screened. FIG. 1B, Chemical structure of the RCM-1 compound. FIG. 1C, RCM-1 decreased nuclear GFP-FOXM1 fluorescence. U2OS C3 cells were fixed and scanned for GFP (green) using scanning PerkinElmer Opera imaging system. Random images (n=12) were taken for each cell culture. DNA stain (red) and a phase contrast were used to identify boundary of nuclei and cytoplasm in individual cells. FIG. 1D, Nuclear/cytoplasmic GFP ratio in U2OS C3 cells is shown as mean±SD (n=200 cells). FIG. 1E, Different concentrations of the RCM-1 compound were used to determine EC50. FIG. 1F, Western blots show amounts of endogenous FOXM1 protein and other transcription factors in RCM-1-treated human airway epithelial cells cultured on air-liquid interface. FIG. 1G, Decreased mRNAs of FOXM1 target genes (Cdc25B and Plk1) were found in RCM-1-treated cells by qRT-PCR (** indicates p<0.01). Cdc25A mRNA was not changed. FIG. 1H, RCM-1 increases ubiquitination of FOXM1 isoforms (shown by arrows). Immunoprecipitation was performed in A549 cell lysates using FOXM1 antibody followed by Western blot with ubiquitin antibodies. * indicates the location of IgG on Western blot. FIG. 1I-FIG. 1J, RCM-1 induces the translocation of endogenous FOXM1 from cell nuclei to cytoplasm (red fluorescence). FOXM1 co-localizes with ubiquitin and proteosomal marker protein PSMA5 in proteasomes of RCM-1 treated cells. DAPI nuclear stain was used to visualize cell nuclei. Immunostaining was performed in A549 cells.

FIG. 2A, RCM-1 inhibits FOXM1 in the mouse lung. BALB/c mice were treated with either RCM-1 or vehicle three times with 48 hr intervals. Total lung protein was prepared 24 hr after the last RCM-1 administration and analyzed by Western blot for endogenous FOXM1 and β-actin. FIG. 2B, GFP-FOXM1 transgenic mice were given Dox to activate transgene. 24 hr later, mice were treated with either RCM-1 or vehicle for 2 weeks (i.p. with 48-hr intervals). Frozen lung sections were analyzed for GFP fluorescence. RCM-1 reduces nuclear GFP-FOXM1 in bronchiolar epithelium. Magnification is ×680. FIG. 2C, RCM-1 inhibits GFP-FOXM1 after HDM challenge. Tissue samples were prepared from lungs of Dox-treated GFP-FOXM1 transgenic (TG) mice 24 h after HDM challenge. RCM-1 was given 3 times as described in Supplemental materials. Dox-treated CCSP-rtTA (WT) mice were used as controls. Lung sections were stained with antibodies recognizing human (transgenic) FOXM1 (dark brown) but not mouse FoxM1 protein. Slides were counterstained with nuclear fast red (red). Scale bars are 50 μm. FIG. 2D, Western blot shows that RCM-1 decreases GFP and FOXM1 proteins in HDM-treated GFP-FOXM1 mice. FIG. 2E, RCM-1 inhibits GFP fluorescence in GFP-FOXM1 TG mice treated with HDM. Frozen lung sections were analyzed for GFP fluorescence. Scale bars: left and middle panels, 50 μm; right panels, 5 μm.

FIG. 3A, Experimental protocol showing the treatment of BALB/c mice with HDM and RCM-1. HDM was given by intranasal administration on days 0 and 14. RCM-1 was given by intraperitoneal injection on days 13, 15 and 16. FIG. 3B, RCM-1 ameliorated airway hyperreactivity induced by HDM. FlexiVent system was used to measure airway mechanics. *p<0.05, **p<0.01.

FIG. 4A, H&E and Alcian blue staining show reduced numbers of goblet cells in mice treated with RCM-1. HDM was given to BALB/c mice by intranasal administration on days 0 and 14. RCM-1 was given by intraperitoneal injection on days 13, 15 and 16. Lungs were harvested 72 h after the last HDM challenge. Scale bars are 50 μm. FIG. 4B, Immunostaining shows decreased expression of SPDEF, MUC5AC and FOXM1 after RCM-1 treatment of HDM-challenged mice. Scale bars are 50 μm. FIG. 4C, qRT-PCR of total lung RNA. HDM treatment increased mRNA levels of Foxm1, Spdef, Foxa3, Agr2, Muc5ac and decreased expression of Foxa2. RCM-1 reversed the effects of HDM on mRNA levels of these genes. Data are shown as means±standard errors of the means (SEM) (n=3 mice/group). *, p<0.05; **, p<0.01.

FIG. 5A, RCM-1 did not affect the number of inflammatory cells in BALF. HDM was given to BALB/c mice by intranasal administration on days 0 and 14. RCM-1 was given by intraperitoneal injection on days 13, 15 and 16. BALF was obtained at 72 hr after the last HDM challenge. Five hundred cells were counted to calculate the percentage of inflammatory cells. (n=6 mice/group; *, p<0.05; , p<0.01, *, p<0.001). FIG. 5B, Histological assessment of lung tissue. Lung sections were stained with hematoxylin and eosin and examined. Histological scores included the degree of inflammatory cell infiltration of the bronchiolar wall, goblet cell metaplasia, vascular thickening, perivascular infiltrate, smooth muscle hyperplasia, thickening of alveolar septa and peribronchiolar fibrosis. See Tables 2 and 3.

FIG. 6A-FIG. 6B, RCM-1 decreased goblet cell metaplasia after administration of IL-13. Lung paraffin sections were stained with H&E and Alcian blue (6A) or used for immunostaining for FOXM1, SPDEF and MUC5AC (6B). Scale bars are 50 µm. FIG. 6C, RCM-1 did not change the number of inflammatory cells in BALF of IL-13-treated mice (n=5 mice were used in each group). Data are shown as means±standard errors of the means (SEM). FIG. 6D, FlexiVent system was used to measure airway mechanics. RCM-1 inhibited IL-13-mediated airway hyperreactivity and increased lung compliance in IL-13 treated mice (n=5 mice per group). FIG. 6E, RCM-1 inhibits expression of genes associated with goblet cell metaplasia. qRT-PCR of total lung RNA shows expression levels of Foxm1, Spdef, Foxa3, Foxa2, Scgb1a1, Agr2 and Muc5ac (n=4). *, p<0.05; **, p<0.01.

FIG. 7A-FIG. 7B, qRT-PCR shows altered expression of genes in RCM-1-treated lungs. qRT-PCR was performed on total lung RNA (n=4). IL-13 was given to BALB/c mice on days 1, 3 and 4. FIG. 7C, The Luminex Multiplex assay was used to measure the concentrations of IFNγ, IL-4, IL-5 and IL-33 in BALF (n=5). Data are shown as means±standard errors of the means (SEM). *, p<0.05; **, p<0.01. D-F, RCM-1 inhibits FOXM1, pERK1/2 and total ERK but does not change IL-13-induced phosphorylation of STAT6. Western blot was performed using total protein extract from mouse lung tissue (FIG. 7D), human airway epithelial cells (FIG. 7E) and A549 cells (FIG. 7F). RCM-1 was added to cell cultures for 24 hr.

FIG. 8A-FIG. 8E. RCM-1 inhibits FOXM1 in U2OS cells and pulmonary airways. (FIG. 8A-FIG. 8C) Images show nuclei and cell boundaries in U2OS C3 reporter cells treated with Dox. Scanning PerkinElmer Opera imaging system was used to measure GFP in nuclei and cytoplasm of 200 randomly selected cells. Nuclear/cytoplasmic GFP ratios were determined for each individual cell. Statistical significance is shown as mean±standard deviation (FIG. 8B) and Z values (FIG. 8C) calculated from 30 different cell culture plates. (FIG. 8D) Schematic diagram shows a Dox-inducible system in CCSP-rtTA/tetO7-CMV-GFP-FOXM1 double transgenic mice (GFP-FOXM1 mice). (FIG. 8E) RCM-1 inhibits the GFP-FOXM1 transgene in bronchiolar epithelium. GFP-FOXM1 mice were given Dox to activate transgene. 24-hr later, mice were treated with either RCM-1 or vehicle for 2 weeks (i.p. with 48-hr intervals). RCM-1 decreased immunostaining for FOXM1 and GFP. CCSP and FOXA2 were not changed. Magnification is ×200 (inserts, ×400).

(FIG. 9A) BALB/c mice were treated with either RCM-1 or vehicle three times with 48 hr intervals. Blood serum was obtained 24 hr after the last RCM-1 administration. Serological test shows that RCM-1 did not affect the liver enzymes ALT and AST, blood urea nitrogen (BUN), creatine phosphokinase (CPK), alkaline phosphatase (ALP), albumin and total protein in blood serum (n=4 mice per group; *, P<0.05; **, P<0.01). Data are shown as means±standard errors of the means (SEM). (FIG. 9B) H&E staining shows that RCM-1 did not change histology of the intestine. Magnification: upper panels, ×100; bottom panels, ×400.

(FIG. 10A) Lung paraffin sections were immunostained for FOXA2 and CCSP (dark brown). Slides were counterstained with nuclear fast red (red). HDM was given to BALB/c mice by intranasal administration on days 0 and 14. RCM-1 was given by intraperitoneal injection on days 13, 15 and 16. Lungs were harvested 72 h after the last HDM challenge. Scale bars are 50 µm. (FIG. 10B) Images show the presence of inflammatory cells in BALF obtained from mice treated with HDM or saline. Magnification is ×200.

(FIG. 11A) Experimental protocol shows the treatment of BALB/c mice with RCM-1 and recombinant mouse IL-13. IL-13 was given by intranasal administration on days 1, 3 and 4. RCM-1 was given by i.p. injection on days 0, 2 and 4. Mice were sacrificed on day 5. (FIG. 11B) Lung paraffin sections were used for immunostaining with FOXA2 antibodies (brown). Slides were counterstained with nuclear fast red (red). Scale bars are 50 µm.

Figure 1A:
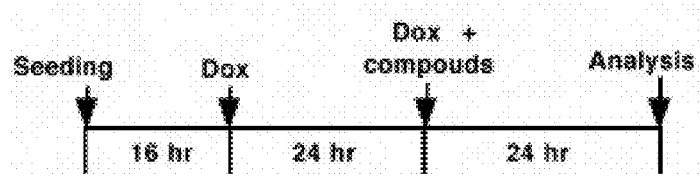
FIG. 1A-1J. Identification of the FOXM1 inhibitor RCM-1 by high-throughput screening.

RCM-1 was added to cell cultures for 24 hr. RCM-1 inhibits FOXM1 but does not change pSTAT6 and total STAT6 in nuclear and cytoplasmic extracts. Lamin A/C shows the purity of nuclear and cytoplasmic fractions.

DETAILED DESCRIPTION OF THE INVENTION

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms and expressions used herein have the ordinary meaning as is accorded to such terms and expressions with respect to their corresponding respective areas of inquiry and study except where specific meanings have otherwise been set forth herein.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms refer to children.

"Therapeutically effective amount" relates to the amount or dose of an active compound or composition described herein that will lead to one or more therapeutic effect, in particular desired beneficial effects. A therapeutically effective amount of a substance can vary according to factors such as the disease state, age, sex, and weight of the subject, and the ability of the substance to elicit a desired response in the subject. Dosage regime may be adjusted to provide the optimum therapeutic response. For example, several divided doses may be administered daily or the dose may be proportionally reduced as indicated by the exigencies of the therapeutic situation.

The phrase "pharmaceutically acceptable," as used in connection with compositions of the disclosure, refers to molecular entities and other ingredients of such compositions that are physiologically tolerable and do not typically produce untoward reactions when administered to a subject (e.g., human). In certain embodiments, as used herein, the term "pharmaceutically acceptable" means approved by a regulatory agency of a Federal or a state government or listed in the U.S. Pharmacopeia or other generally recognized pharmacopeia for use in mammals (e.g., humans).

The term "carrier" applied to pharmaceutical compositions of the disclosure refers to a diluent, excipient, or vehicle with which an active compound (e.g., dextromethorphan) is administered. Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, sesame oil and the like. Suitable pharmaceutical carriers are described in "Remington's Pharmaceutical Sciences" by E. W. Martin, 18th Edition.

The term "compound," as used herein, is also intended to include any salts, solvates, or hydrates thereof.

The terms "pharmaceutically acceptable salts" or "a pharmaceutically acceptable salt thereof" refer to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as The Merck Index. Any suitable constituent can be selected to make a salt of an active drug discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives of dextromethorphan and/or quinidine can also be suitable for use in the compositions and methods disclosed herein. In certain embodiments, the dextromethorphan is administered in the form of dextromethorphan hydrobromide, and the quinidine is administered in the form of quinidine sulfate. A salt of a compound of this disclosure may be formed between an acid and a basic group of the compound, such as an amino functional group, or a base and an acidic group of the compound, such as a carboxyl functional group. According to another embodiment, the compound is a pharmaceutically acceptable acid addition salt. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In one aspect, a composition comprising

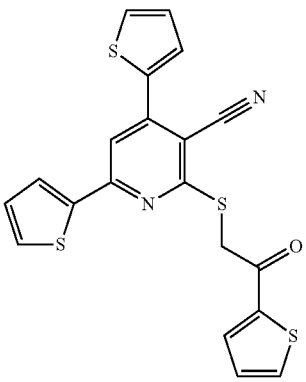 [SMILES: N#Cc1c(-c2cccs2)cc(-c2cccs2)nc1SCC(=O)c1cccs1]

(Compound I, also referred to herein interchangeably as "RCM-1"), or a pharmaceutically acceptable salt thereof; and a pharmaceutically acceptable excipient is disclosed.

In one aspect, Compound I or a pharmaceutically acceptable salt thereof, may be present in an amount of from about 0.5% to about 95%, or from about 1% to about 90%, or from about 2% to about 85%, or from about 3% to about 80%, or from about 4%, about 75%, or from about 5% to about 70%, or from about 6%, about 65%, or from about 7% to about 60%, or from about 8% to about 55%, or from about 9% to about 50%, or from about 10% to about 40%, by weight of the composition.

In one aspect, the composition may be useful for the treatment, prevention, or amelioration of a symptom of an airway disorder. The airway disorder, in some aspects, may be characterized by one or more conditions selected from goblet cell metaplasia, lung tissue inflammation, increased airway hyperresponsiveness, mucus hyperplasia, decreased airway resistance, increased production of pro-inflammatory cytokines, or combinations thereof.

In one aspect, the airway disorder may be selected from asthma, chronic obstructive pulmonary disease (COPD), cystic fibrosis (CF), allergic disorders, pulmonary inflammatory diseases, pulmonary fibrosis, interstitial lung diseases, or a combination thereof.

In one aspect, the composition may be administered in an amount sufficient to reduce one or more indices of airway dysfunction selected from inflammatory cell infiltration, vascular thickening/perivascular infiltration, goblet cell metaplasia, alveolar septa thickening, smooth muscle hypertrophy/hyperplasia, peribronchiolar fibrosis, lung tissue inflammation, airway hyperresponsiveness, mucus hyperplasia, decreased lung compliance, increased airway resistance, pro-inflammatory cytokine production, or a combination thereof.

In one aspect, the compound may be present in an amount sufficient to inhibit FOXM1 in an individual upon administration of said composition to said individual.

Methods

In one aspect, a method of treating a lung condition is disclosed. In this aspect, the lung condition may be selected from asthma, chronic obstructive pulmonary disease (COPD), cystic fibrosis (CF), allergic disorders, pulmonary inflammatory diseases, pulmonary fibrosis, interstitial lung diseases, and the method may comprise the step of administering to a subject in need thereof a therapeutically effective amount of the disclosed compositions.

In one aspect, the Compound 1 may be administered in an amount sufficient to reduce FOXM1 activity, wherein said FOXM1 expression may be measured one or more methods known to one of ordinary skill in the art. Exemplary methods that may be used include, but are not limited to immunostaining of lung tissue sections, measurement of Foxm1 mRNA, measurement of protein levels obtained from a lung biopsy or other tissue collection. A combination of methods may be used to determine FOXM1 expression.

In one aspect, administration of the composition may be in an amount sufficient to reduce one or more symptoms selected from inflammatory cell infiltration, vascular thickening/perivascular infiltration, goblet cell metaplasia, alveolar septa thickening, smooth muscle hypertrophy/hyperplasia, peribronchiolar fibrosis, lung tissue inflammation, airway hyperresponsiveness, mucus hyperplasia, decreased lung compliance, increased airway resistance, pro-inflammatory cytokine production, or a combination thereof.

In one aspect, the composition may be administered via the airway as an aerosol. In a further aspect, the composition may be administered sub-cutaneously. In a yet further aspect, the composition may be administered via a nanoparticle-based delivery system. Such methods are readily understood by one of ordinary skill in the art.

In a further aspect, a kit is disclosed. The kit may comprise a composition as disclosed herein and a means for delivery of the composition to a human.

Further disclosed is an article of manufacture that may comprise a container comprising a label; and a composition as disclosed herein. In certain aspects, the label may indicate that the composition is to be administered to a human having, suspected of having, or at risk for developing, a lung condition selected from asthma, chronic obstructive pulmonary disease (COPD), cystic fibrosis (CF), allergy, or a combination thereof. The label may further comprise instructions as to amounts and/or a dosage schedule for administration of the composition. In another aspect, the label may indicate that the composition is to be administered to a human having or at risk for developing a symptom selected from inflammatory cell infiltration, vascular thickening/perivascular infiltration, goblet cell metaplasia, alveolar septa thickening, smooth muscle hypertrophy/hyperplasia, peribronchiolar fibrosis, lung tissue inflammation, airway hyperresponsiveness, mucus hyperplasia, decreased lung compliance, increased airway resistance, pro-inflammatory cytokine production, or a combination thereof.

Dosage

As will be apparent to those skilled in the art, dosages outside of these disclosed ranges may be administered in some cases. Further, it is noted that the ordinary skilled clinician or treating physician will know how and when to interrupt, adjust, or terminate therapy in consideration of individual patient response.

In certain embodiment, the dosage of the composition provided herein, based on weight of the active compound, administered to prevent, treat, manage, or ameliorate a disorder, or one or more symptoms thereof in a subject may be at least about 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of about 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The compositions may be administered in oral dosage forms such as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular forms all utilizing dosage forms well known to those of ordinary skill in the pharmaceutical arts. The compositions may be administered by intranasal route via topical use of suitable intranasal vehicles, or via a transdermal route, for example using conventional transdermal skin patches. A dosage protocol for administration using a transdermal delivery system may be continuous rather than intermittent throughout the dosage regimen.

A dosage regimen will vary depending upon known factors such as the pharmacodynamic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect. The effective amount of a drug required to prevent, counter, or arrest progression of a condition can be readily determined by an ordinarily skilled physician The pharmaceutical compositions may include suitable dosage forms for oral, parenteral (including subcutaneous, intramuscular, intradermal and intravenous), transdermal, sublingual, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. Oral preparations include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. For topical or nasal administration, penetrants or permeation agents that are appropriate to the particular barrier to be permeated are used in the formulation. Such penetrants are generally known in the art. The pharmaceutical compositions are prepared by conventional techniques appropriate to the desired preparation containing appropriate amounts of the active ingredient, that is, the compound of Compound I according to the invention.

The dosage of the compound of Compound I to achieve a therapeutic effect will depend not only on such factors as the age, weight and sex of the patient and mode of administration, but also on the degree of FoxM1 inhibition desired and the potency of the compound of Compound I for the particular disorder or disease concerned. It is also contemplated that the treatment and dosage of the compound of Compound I may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

Routes of Administration

Any suitable route of administration can be employed for providing the patient with an effective dosage of the disclosed compositions. For example, oral, rectal, transdermal, parenteral (subcutaneous, intramuscular, intravenous), intrathecal, topical, inhalable, and like forms of administration can be employed. Suitable dosage forms include tablets, troches, dispersions, suspensions, solutions, capsules, patches, and the like. Administration of medicaments prepared from the compounds described herein can be by any suitable method capable of introducing the compounds into the bloodstream. In some embodiments, the formulations can contain a mixture of active compounds with pharmaceutically acceptable carriers or diluents known to those of skill in the art.

The compositions can be prepared in any desired form, for example, tables, powders, capsules, injectables, suspensions, sachets, cachets, patches, solutions, elixirs, and aerosols. Carriers such as starches, sugars, microcrystalline cellulose, diluents, granulating agents, lubricants, binders, disintegrating agents, and the like can be used in oral solid preparations. In certain embodiments, the compositions are prepared as oral solid preparations (such as powders, capsules, and tablets). In certain embodiments, the compositions are prepared as oral liquid preparations. In some embodiments, the oral solid preparations are tablets. If desired, tablets can be coated by standard aqueous or non-aqueous techniques.

In addition to the dosage forms set out above, the compounds disclosed herein can also be administered by sustained release, delayed release, or controlled release compositions and/or delivery devices.

Pharmaceutical compositions suitable for oral administration can be provided as discrete units such as capsules, cachets, sachets, patches, injectables, tablets, and aerosol sprays, each containing predetermined amounts of the active ingredients, as powder or granules, or as a solution or a suspension in an aqueous liquid, a non-aqueous liquid, an oil-in-water emulsion, or a water-in-oil liquid emulsion. Such compositions can be prepared by any of the conventional methods of pharmacy, but the majority of the methods typically include the step of bringing into association the active ingredients with a carrier which constitutes one or more ingredients. In general, the compositions are prepared by uniformly and intimately admixing the active ingredients with liquid carriers, finely divided solid carriers, or both, and then, optionally, shaping the product into the desired presentation.

For example, a tablet can be prepared by compression or molding, optionally, with one or more additional ingredients. Compressed tablets can be prepared by compressing in a suitable machine the active ingredient in a free-flowing form such as powder or granules, optionally mixed with a binder, lubricant, inert diluent, surface active or dispersing agent. Molded tablets can be made by molding, in a suitable machine, a mixture of the powdered compound moistened with an inert liquid diluent.

A composition or formulation may be administered to a subject continuously or periodically.

The compositions or fractions thereof typically comprise suitable pharmaceutical diluents, excipients, vehicles, or carriers selected based on the intended form of administration, and consistent with conventional pharmaceutical practices. The carriers, vehicles etc. may be adapted to provide an additive, synergistically effective or therapeutically effective amount of the active compounds. Suitable pharmaceutical diluents, excipients, vehicles, and carriers are described in the standard text, Remington: The Science and Practice of Pharmacy (21st Edition. 2005, University of the Sciences in Philadelphia (Editor), Mack Publishing Company), and in The United States Pharmacopeia: The National Formulary (USP 24 NF 19) published in 1999. By way of example, for oral administration in the form of a capsule or tablet, the active components can be combined with an oral, non-toxic pharmaceutically acceptable inert carrier such as lactose, starch, sucrose, methyl cellulose, magnesium stearate, glucose, calcium, sulfate, dicalcium phosphate, mannitol, sorbital, and the like. For oral administration in a liquid form, the agents may be combined with any oral, non-toxic, pharmaceutically acceptable inert carrier such as ethanol, glycerol, water, and the like. Suitable binders (e.g. gelatin, starch, corn sweeteners, natural sugars including glucose; natural and synthetic gums, and waxes), lubricants (e.g. sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof.

In one aspect, a pharmaceutical composition may have pH from about 7 to 10.

Formulations for parenteral administration of a composition may include aqueous solutions, syrups, aqueous or oil suspensions and emulsions with edible oil such as cottonseed oil, coconut oil or peanut oil. Dispersing or suspending agents that can be used for aqueous suspensions include synthetic or natural gums, such as tragacanth, alginate, acacia, dextran, sodium carboxymethylcellulose, gelatin, methylcellulose, and polyvinylpyrrolidone.

Compositions for parenteral administration may include sterile aqueous or non-aqueous solvents, such as water, isotonic saline, isotonic glucose solution, buffer solution, or other solvents conveniently used for parenteral administration of therapeutically active agents. A composition intended for parenteral administration may also include conventional additives such as stabilizers, buffers, or preservatives, e.g. methylhydroxybenzoate or similar additives.

In an embodiment, a solid form pharmaceutical composition is provided (e.g. tablets, capsules, powdered, or pulverized form) comprising a Compound I.

In another embodiment, a liquid drug formulation is provided and comprises a pharmaceutically acceptable salt of Compound I, and to lyophilized drug formulations that can be reconstituted to provide suspensions that are stable and suitable for parenteral administration.

A composition described herein may be sterilized by, for example, filtration through a bacteria retaining filter, addition of sterilizing agents to the composition, irradiation of the composition, or heating the composition. Alternatively, the compounds and compositions may be provided as sterile solid preparations e.g. lyophilized powder, which are readily dissolved in sterile solvent immediately prior to use.

After pharmaceutical compositions have been prepared, they can be placed in an appropriate container and labeled for treatment of an indicated condition. For administration of a composition, such labeling would include amount, frequency, and method of administration.

Kits

Kits are also provided. In an aspect, a kit comprises or consists essentially of agents or compositions described herein. The kit is a package that houses a container which may contain a composition as disclosed herein, and also houses instructions for administering the agent or composition to a subject. In one aspect, a pharmaceutical pack or kit is provided comprising one or more containers filled with one or more composition as disclosed herein. Associated with such container(s) can be various written materials such as instructions for use, or a notice in the form prescribed by a governmental agency regulating the manufacture, use or sale of pharmaceuticals or biological products, which notice reflects approval by the agency of manufacture, use, or sale for human administration.

As there may be advantages to mixing a component of a composition described herein and a pharmaceutically acceptable carrier, excipient or vehicle near the time of use, the invention encompasses kits in which components of the compositions are packaged separately. For example, the kit can contain an active ingredient in a powdered or other dry form in, for example, a sterile vial or ampule and, in a separate container within the kit, a carrier, excipient, or vehicle, or a component of a carrier, excipient, or vehicle (in liquid or dry form). In an aspect, the kit can contain a component in a dry form, typically as a powder, often in a lyophilized form in, for example, a sterile vial or ampule and, in a separate container within the kit, a carrier, excipient, or vehicle, or a component of a carrier, excipient, or vehicle. Alternatively, the kit may contain a component in the form of a concentrated solution that is diluted prior to administration. Any of the components described herein, any of the carriers, excipients or vehicles described herein, and any combination of components and carriers, excipients or vehicles can be included in a kit.

Optionally, a kit may also contain instructions for preparation or use (e.g., written instructions printed on the outer container or on a leaflet placed therein) and one or more devices to aid the preparation of the solution and/or its administration to a patient (e.g., one or a plurality of syringes, needles, filters, tape, tubing (e.g., tubing to facilitate intravenous administration) alcohol swabs and/or the Band-Aid® applicator). Compositions which are more concentrated than those administered to a subject can be prepared. Accordingly, such compositions can be included in the kits with, optionally, suitable materials (e.g., water, saline, or other physiologically acceptable solutions) for dilution. Instructions included with the kit can include, where appropriate, instructions for dilution.

In other embodiments, the kits can include pre-mixed compositions and instructions for solubilizing any precipitate that may have formed during shipping or storage. Kits containing solutions of Compound I, or a pharmaceutically acceptable salt thereof, and one or more carriers, excipients or vehicles may also contain any of the materials mentioned above (e.g., any device to aid in preparing the composition for administration or in the administration per se). The instructions in these kits may describe suitable indications (e.g., a description of patients amenable to treatment) and instructions for administering the solution to a patient.

EXAMPLES

Asthma is a common chronic pulmonary disorder, associated with mucus hyperproduction, persistent pulmonary inflammation, airway hyperresponsiveness, and tissue remodeling (1, 2). Allergen-induced activation of Th2 lymphocytes, type 2 innate lymphoid cells (ILC2), dendritic cells and eosinophilic infiltration are important components in asthma pathogenesis. In response to allergens, resident and inflammatory cells produce IL-4, IL-5, IL-13, IL-9, IL-17, IL-25, IL-33 and eotaxins that stimulate pulmonary inflammation and cause airway remodeling. (3-6). Canonical Th2-responses are initiated by cytokines and chemokines produced by respiratory epithelial cells, such as thymic stromal lymphopoietin (TSLP), IL-33 and IL-25, that recruit and activate both innate lymphocytes and T-cells to enhance goblet cell metaplasia and inflammation (6). Clinical management of asthma focuses on reducing allergen-mediated lung inflammation and alleviating hyperresponsiveness of peripheral conducting airways (7). There are many mucolytics and agents targeting airway fluid production, but there is a lack of therapeutic agents that directly target transcriptional networks critical for differentiation of mucin-producing goblet cells. Pharmacological targeting of goblet cell transcription factors may provide new therapeutic opportunities for treatment of patients with asthma and other chronic airway diseases.

Goblet cell metaplasia and mucus hypersecretion are important clinical features of asthma, cystic fibrosis and chronic obstructive pulmonary disease (8). In response to allergen sensitization, goblet cells differentiate from nonciliated airway progenitor cells, including basal and Club cells (9-11). Multiple signaling and transcriptional networks influence goblet cell differentiation. These include JAK/STAT6, Notch, EGFR, Ras/ERK1/2 and NF-kB (10, 12, 13).

IL-13 acts through IL-4 receptor to phosphorylate STAT6 and induce goblet cell metaplasia through a transcriptional network activated by SPDEF and FOXA3 and repressed by TTF-1 and FOXA2 transcription factors (14, 15). SPDEF is required for and sufficient to induce airway goblet cell differentiation at baseline and after aeroallergen exposure (14, 15). SPDEF regulates numerous genes, mediating the production of mucins, their glycosylation and intracellular packaging, including Muc5ac, Muc16, Foxa3, Agr2 and glycosyltransferases (15). FOXM1 is a nuclear transcription factor from the Forkhead (FOX) family that is an upstream transcriptional regulator of SPDEF. FOXM1 binds to and activates Spdef promoter activity (16). Genetic deletion of Foxm1 from airway Club cells inhibits SPDEF and prevents goblet cell metaplasia in response to house dust mite allergens (HDM) (16).

In the present study, Applicant has challenged the concept that transcription factors are "undrugable" targets. Using high throughput screen, Applicant identified a novel small molecule compound, RCM-1, that inhibits FOXM1 activity in vitro and in vivo. RCM-1 prevented goblet cell metaplasia, decreased lung inflammation and inhibited airway hyperresponsiveness in response to HDM or recombinant IL-13. The present study provides a direct support for the feasibility of developing novel inhibitors of goblet cell metaplasia for treatment of asthma and other chronic airway disorders associated with mucus hyperproduction.

Results

Figure 1B:
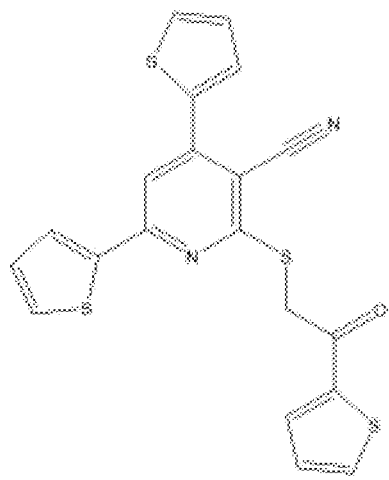
Figure 1C:
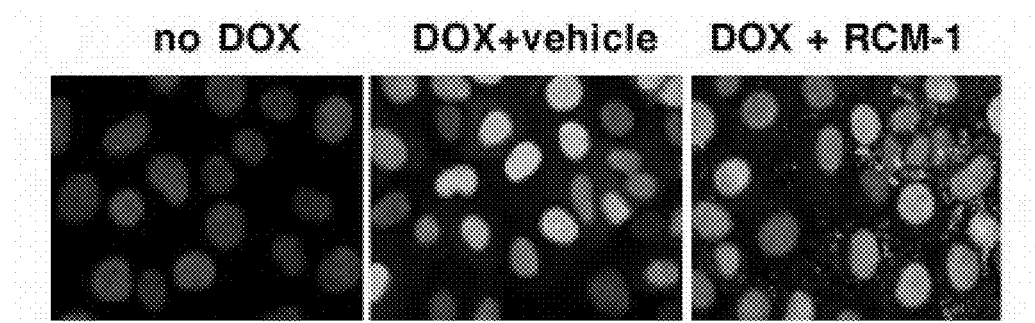
Figure 1D:
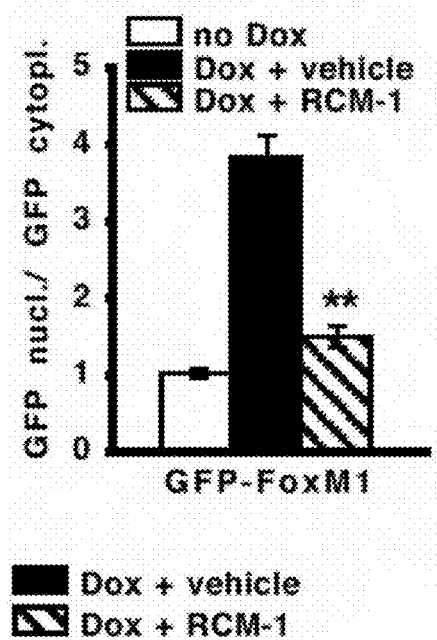
Figure 1E:
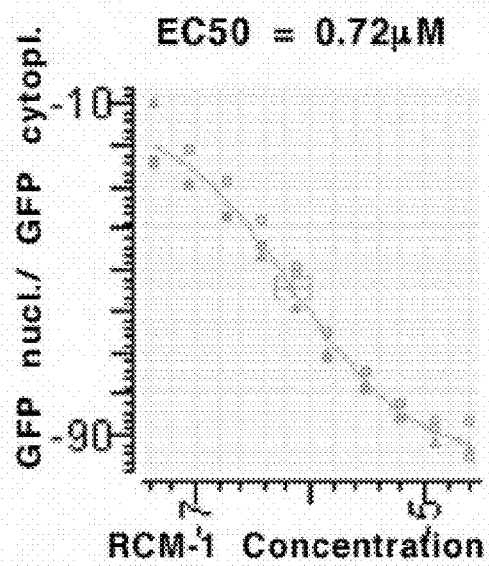
Figure 1F:
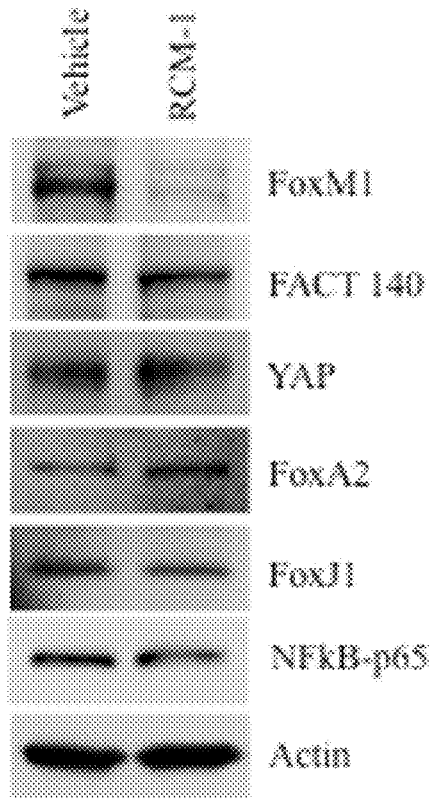
Figure 1G:
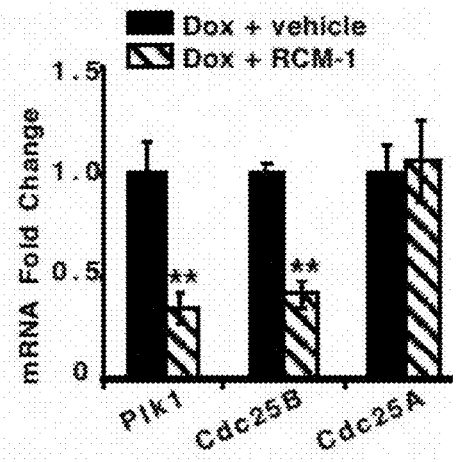
Figure 1H:
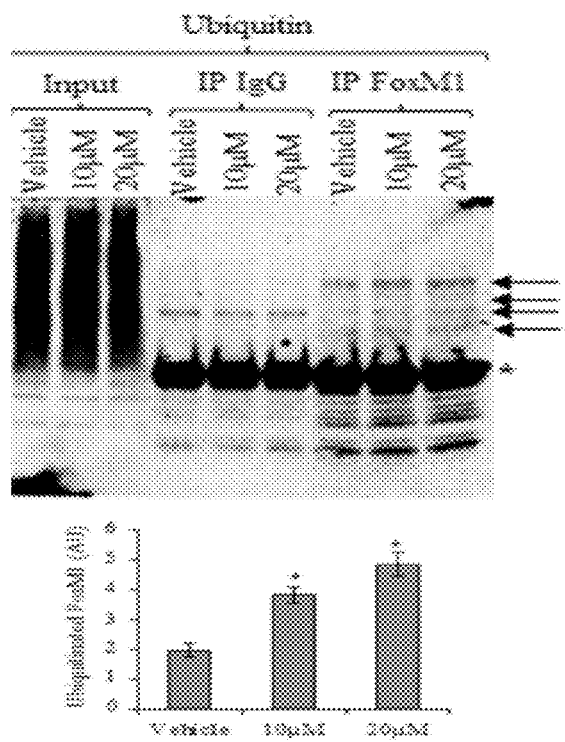
Figure 1I:
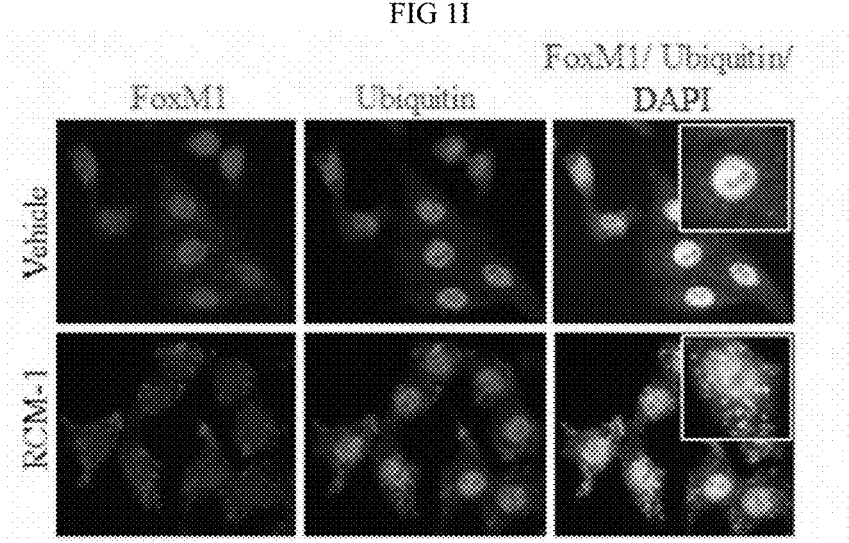
Figure 1J:
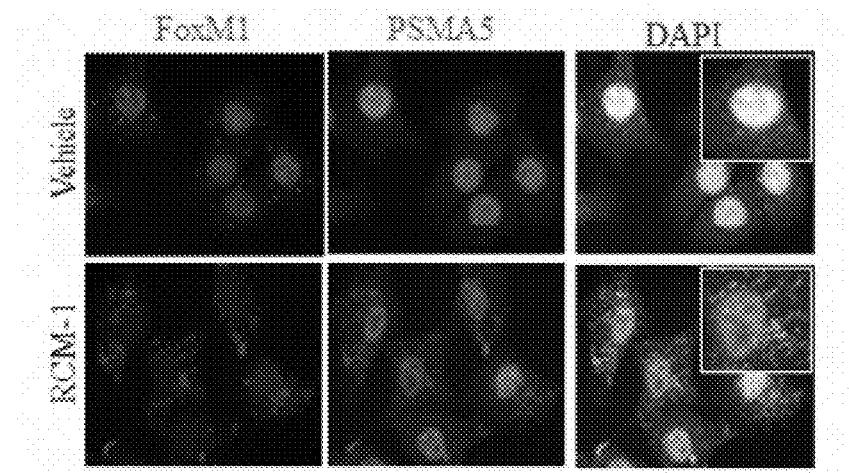
Figure 8A:
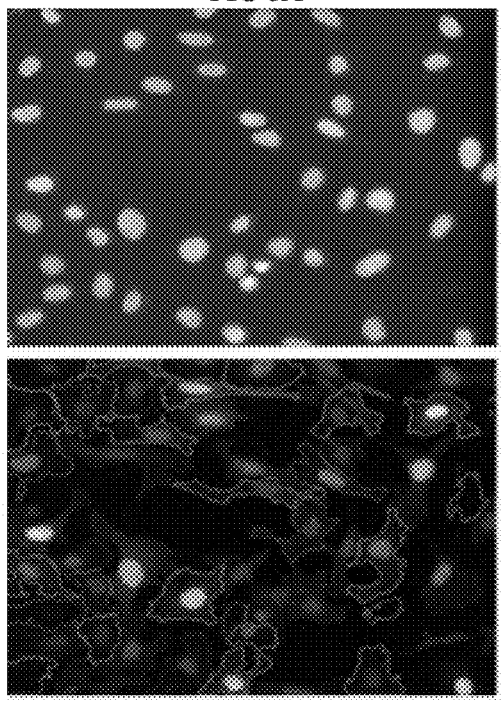
Figure 8B:
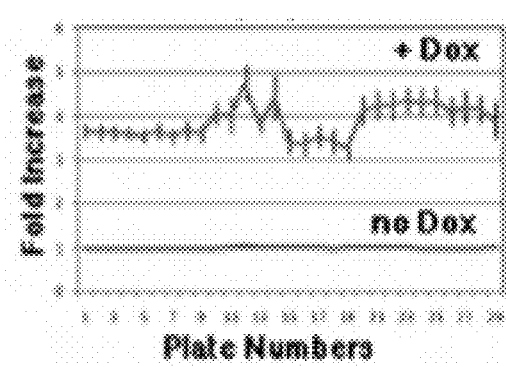
Figure 8C:
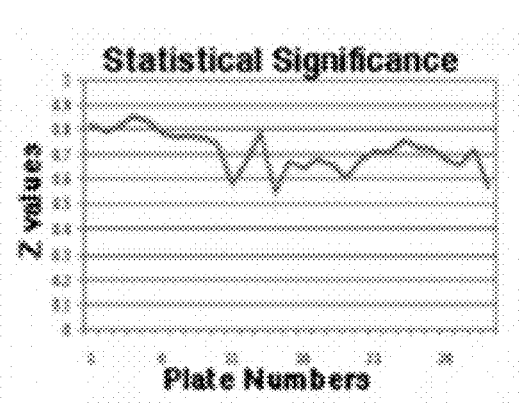
Figure 8D:
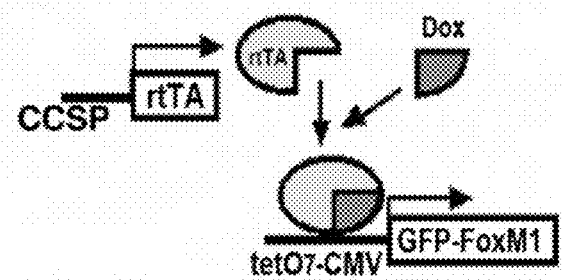
Figure 8D:
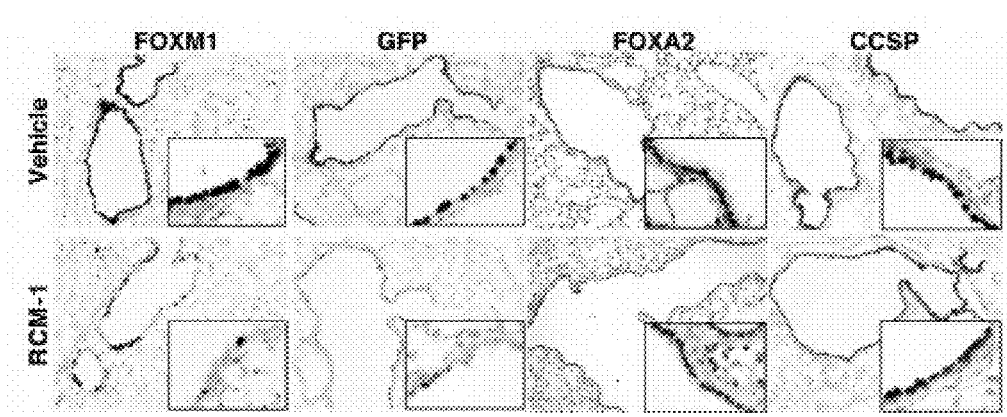

Identification of novel FOXM1 small molecule inhibitor, RCM-1, by high-throughput screen. Since genetic inactivation of Foxm1 gene in airway epithelial cells effectively inhibited goblet cell metaplasia in response to HDM (16), Applicant performed a high-throughput screen to identify novel small molecule compounds inhibiting the FOXM1 protein. The screen was based on the ability of the compounds to inhibit expression and nuclear localization of FOXM1 protein in human osteosarcoma U2OS C3 cell line, in which Doxycycline (Dox) treatment induced expression of the FOXM1 protein fused with GFP reporter (GFP-FOXM1; (17)). U2OS C3 cells were treated with Dox to induce GFP-FOXM1, and 50,000 small molecule compounds were screened for GFP fluorescence (FIG. 1A). Quantitative scanning microscopy was used to measure total GFP and nuclear/cytoplasmic GFP ratios in individual cells (FIG. 8A-C). After identification of GFP-FOXM1-inhibiting compounds, additional dose-response screens were performed to determine EC50. In the present study, Applicant prioritized the nitrile compound RCM-1 (Robert Costa Memorial drug-1, FIG. 1B), named in memory of the late Robert Costa, who originally identified the human FOXM1 (HFH11) gene. RCM-1 inhibited GFP-FOXM1 in U2OS cells with EC50=0.72 µM (FIG. 1C-1E). Furthermore, RCM-1 inhibited expression of FOXM1-target genes Plk1 and Cdc25B (FIG. 1G), a functional readout of FOXM1 transcriptional activity (18). In addition to GFP-FOXM1, the RCM-1 compound inhibited endogenous FOXM1 protein in primary human airway epithelial cells cultured on air-liquid interface (FIG. 1F). Other transcription factors, such as YAP, FACT 140, NF-kB, FOXA2 and FOXJ1, were unaltered by the RCM-1 treatment (FIG. 1F). Finally, RCM-1 inhibited FOXM1 by increasing its ubiquitination and translocation from cell nuclei into proteasomes, as demonstrated by immunoprecipitation of ubiquitinated FOXM1 isoforms (FIG. 1H) and co-localization of FOXM1 with ubiquitin (FIG. 1I) and proteasomal protein PSMA5 (FIG. 1J). Thus, RCM-1 selectively inhibits FOXM1 by increasing the protein degradation.

Figure 2A:
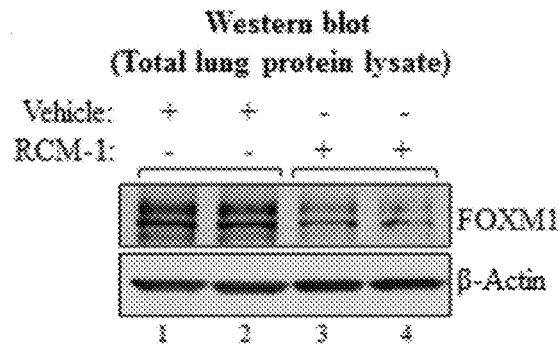
FIG. 2A-FIG. 2E. RCM-1 inhibits FOXM1 in vivo.
Figure 9A:
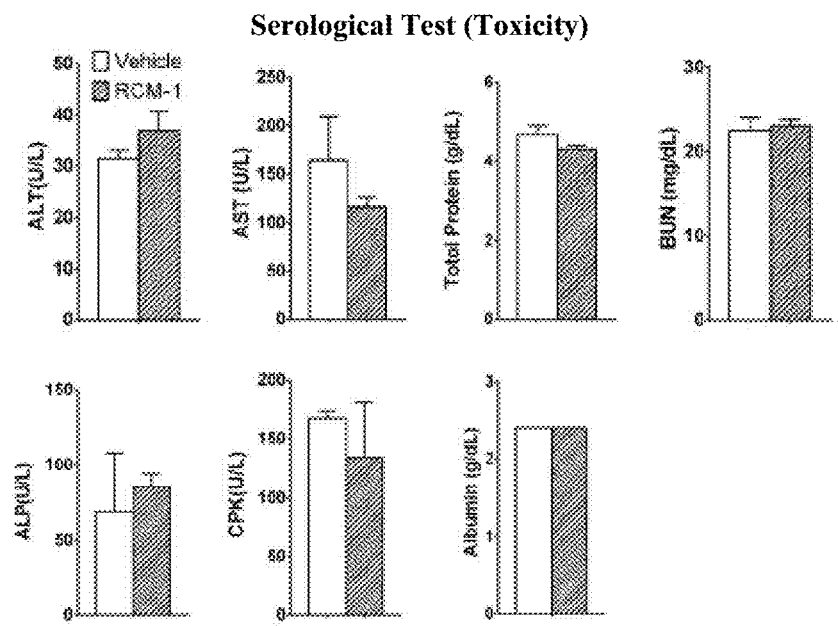
FIG. 9A-FIG. 9B. Lack of toxicity after RCM-1 treatment.
Figure 9B:
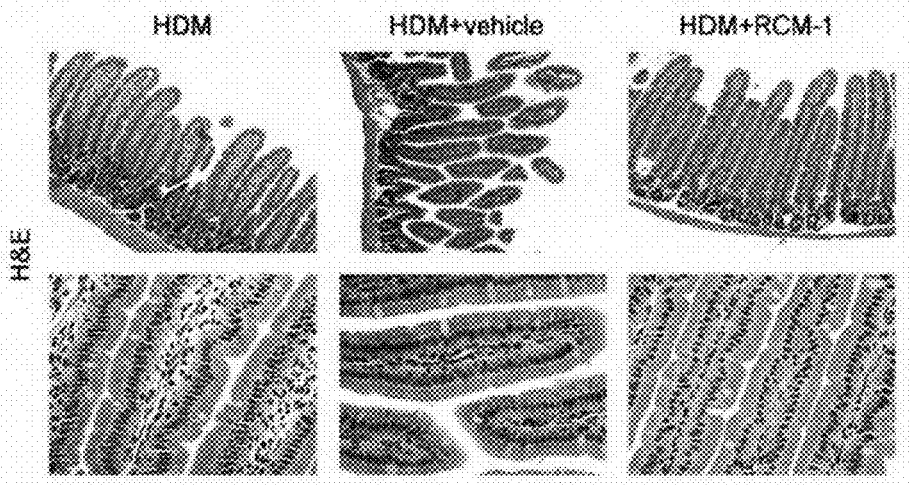

RCM-1 inhibits mouse and human FOXM1 in vivo. The ability of RCM-1 to inhibit FOXM1 in vivo was tested in wild type BALB/c mice. Western blot of lung homogenates demonstrated that RCM-1 treatment decreased endogenous FOXM1 (FIG. 2A). There was no evidence of systemic toxicity as assessed by intestinal morphology or serum concentrations of total protein, albumin, ACT, ALT, ALK, BUN and CPK (FIG. 9A-B).

Figure 2B:
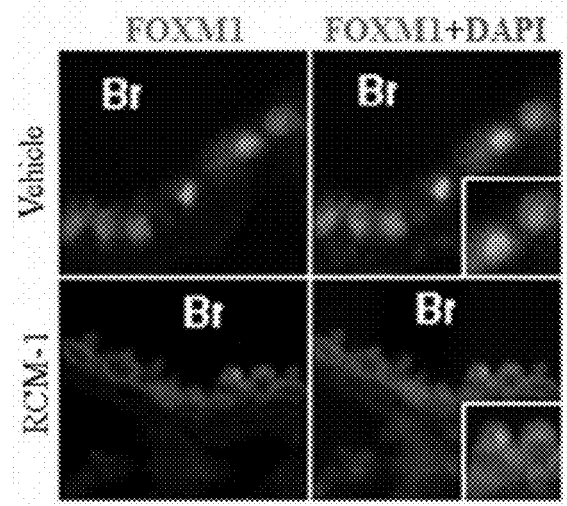
Figure 2C:
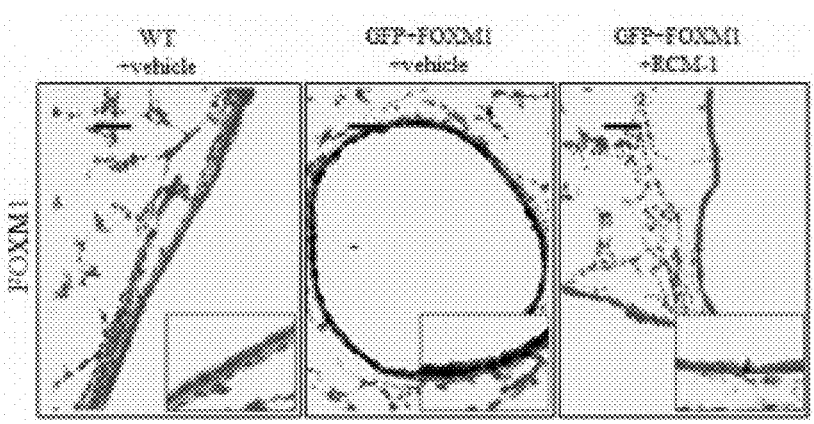
Figure 2D:
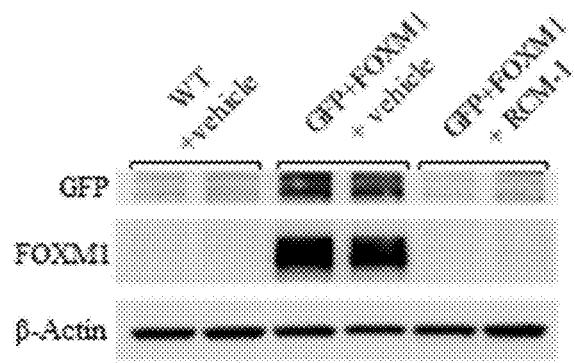
Figure 2E:
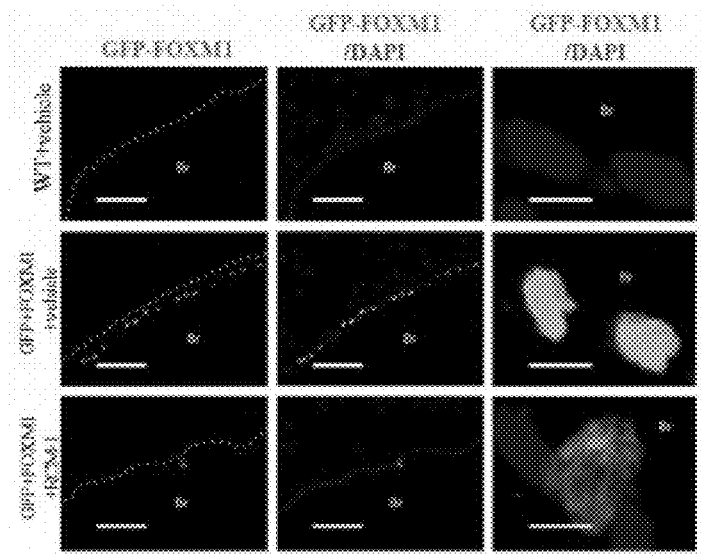

The ability of RCM-1 to inhibit human FOXM1 was tested using transgenic mice that express human FOXM1 fused to GFP (FOXM1-GFP) in airway Club cells (8D and (19)). Immunostaining of lung paraffin sections from GFP-FOXM1 mice demonstrated that RCM-1 reduced both GFP and FOXM1 in airway epithelial cells (8E). RCM-1 excluded GFP-FOXM1 protein from the nuclei of bronchiolar epithelial cells (FIG. 2B), a finding consistent with RCM-1 effects in vitro (FIG. 1C). RCM-1 did not affect expression of CCSP (a Club cell marker) or FOXA2 (FIG. 8E), the latter is a transcription factor with structural similarity to FOXM1. Furthermore, RCM-1 inhibited amounts and nuclear localization of GFP-FOXM1 transgenic protein in mice sensitized to the aeroallergen house dust mite extract (HDM) as shown by immunostaining for FOXM1 (FIG. 2C), Western blot (FIG. 2D) and GFP fluorescence (FIG. 2E). Thus, RCM-1 effectively and selectively inhibited mouse and human FOXM1 proteins in vitro and in vivo.

Figure 3A:
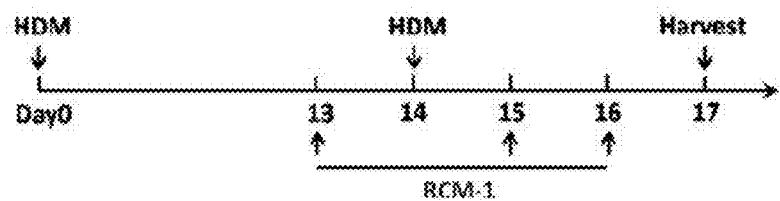
FIG. 3A-FIG. 3B. RCM-1 inhibits HDM-induced airway hyperreactivity.
Figure 3B:
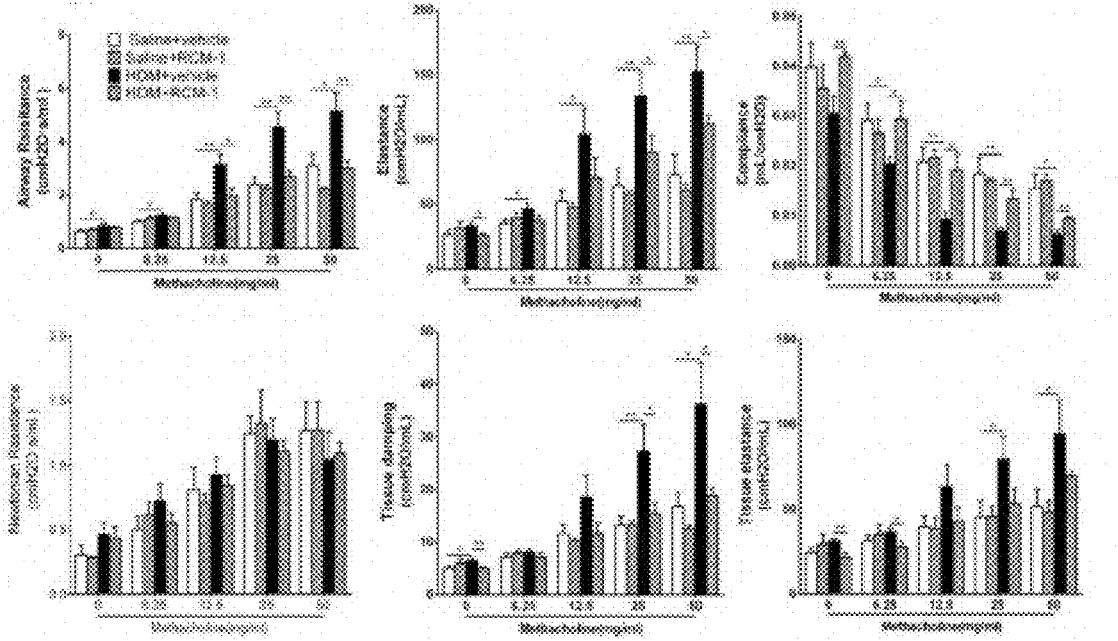

RCM-1 inhibits goblet cell metaplasia and decreases airway resistance following HDM exposure. Since genetic inactivation of Foxm1 protected mice from HDM-mediated pulmonary allergic responses (16), we tested the efficacy of RCM-1 in mice sensitized to HDM. BALB/c mice were subjected to the HDM sensitization/challenge protocol and treated with RCM-1 (FIG. 3A). Consistent with previous studies (16, 20), HDM exposure increased airway resistance, elastance and tissue damping, and decreased pulmonary compliance (FIG. 3B). RCM-1 protected lungs from HDM-induced airway hyperreactivity and preserved lung function (FIG. 3B).

Figure 4A:
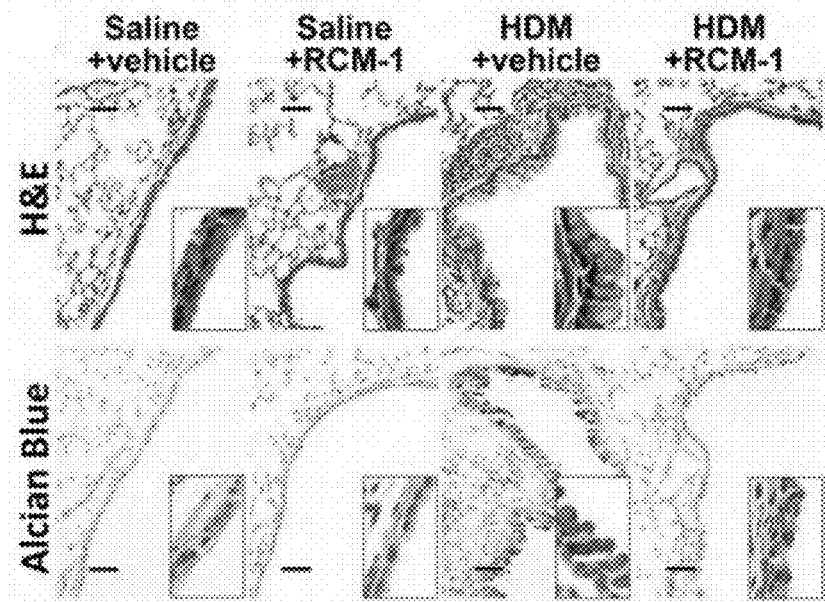
FIG. 4A-FIG. 4C. RCM-1 prevents goblet cell metaplasia in HDM-treated mice.
Figure 4B:
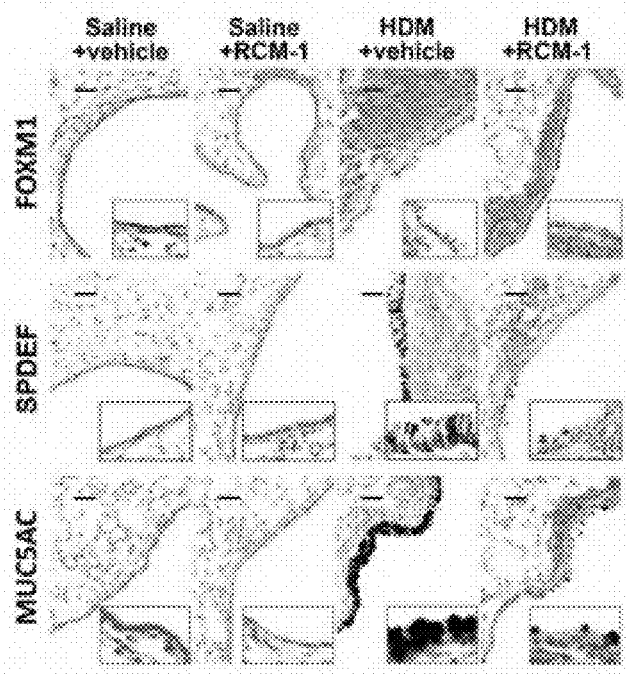
Figure 4C:
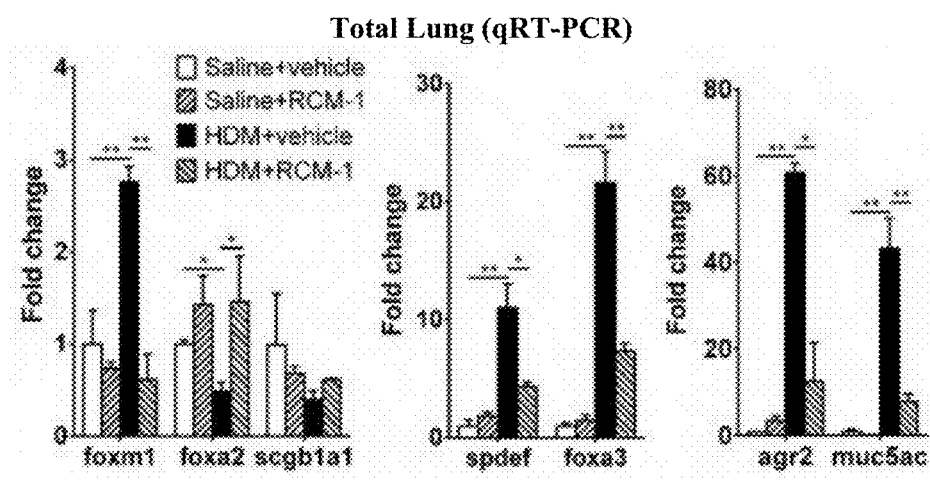
Figure 10A:
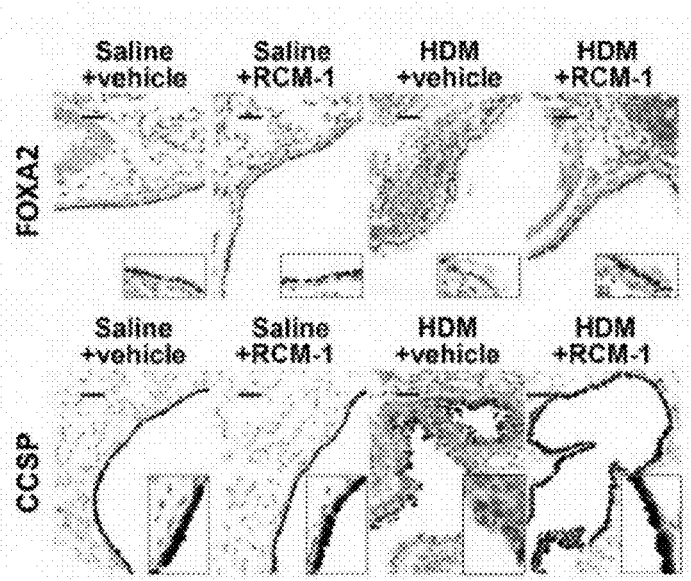
FIG. 10A-FIG. 10B. RCM-1 protects bronchiolar epithelial cells from HDM-mediated inhibition of FOXA2 and CCSP.

Goblet cell metaplasia was inhibited by RCM-1 as shown by H&E and Alcian blue staining (FIG. 4A). RCM-1 decreased FOXM1 staining and mRNA in response to HDM exposure (FIG. 4B-4C). RCM-1 inhibited mRNA and protein levels of MUC5AC, AGR2, and transcription factors SPDEF and FOXA3 (FIG. 4B-4C), known regulators of goblet cell metaplasia (15). In contrast, RCM-1 increased FOXA2 staining and mRNA (FIGS. 4C and 10A) and restored the number of CCSP-positive Club cells in HDM-exposed airways (FIG. 10A). Thus, RCM-1 inhibited goblet cell metaplasia and decreased airway resistance in response to HDM exposure.

Figure 5A:
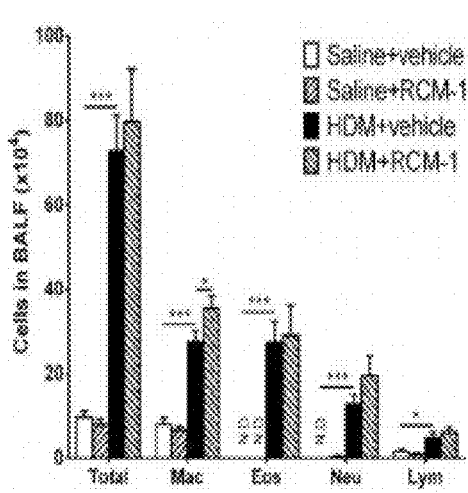
FIG. 5A-FIG. 5B. Effects of RCM-1 on HDM-mediated lung inflammation.
Figure 5B:
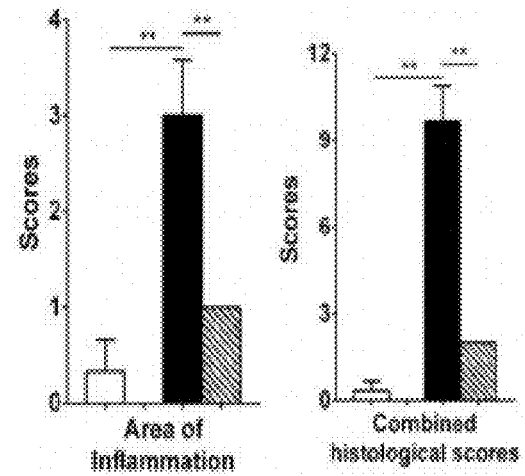
Figure 10B:
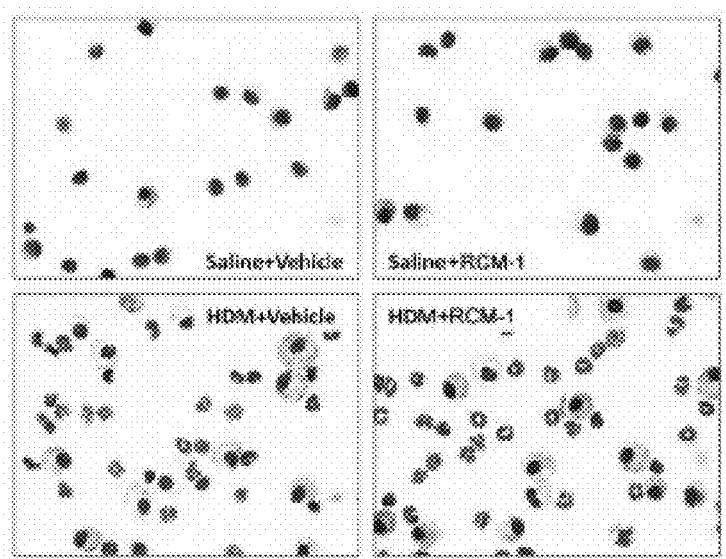

RCM-1 decreases HDM-mediated inflammation in the lung tissue. Consistent with previous studies (16, 20), pulmonary HDM exposure increased the total count and differential counts of inflammatory cells in broncho-alveolar lavage fluid (BALF) (FIG. 5A). Although RCM-1 did not influence the numbers of inflammatory cells in BALF (FIG. 5A and FIG. 10B), histological assessment of the lung tissue demonstrated reduced peribronchial and perivascular infiltration by inflammatory cells and decreased alveolar thickening (FIG. 5B and Table 2 and 3).

Figure 5C:
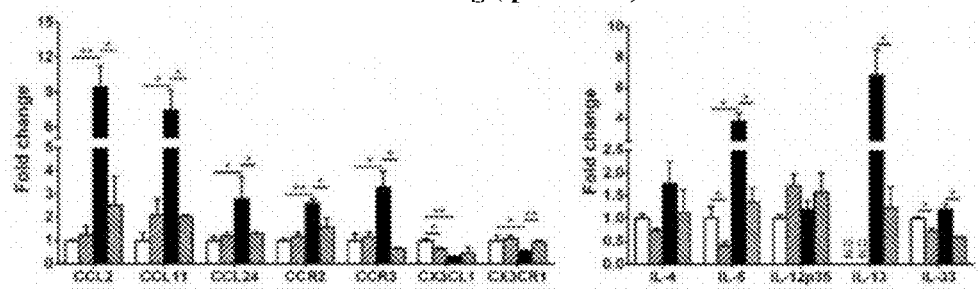
FIG. 5C-FIG. 5D, qRT-PCR was performed on total lung RNA to examine chemokines and cytokines, including those mediating dendritic cell activation (IL-12p35, IL-33), Th2 cytokines (IL-4, IL-5, IL-13), eosinophilic chemoattractants (Ccr3, Ccl11, Ccl24), macrophage chemoattractants (Ccr2, Ccl2, Cx3cl1, Cx3cl1) and bronchoconstrictors (Acta2, Ptgs2, Ltc4s). mRNAs were normalized using β-actin mRNA (n=3 mice per group; *, p<0.05; **, p<0.01).
Figure 5D:
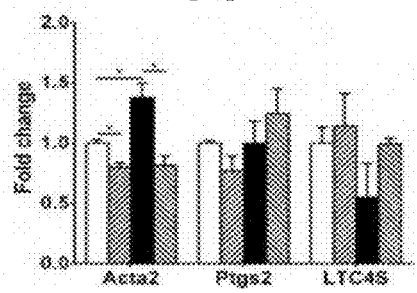
Figure 5E:
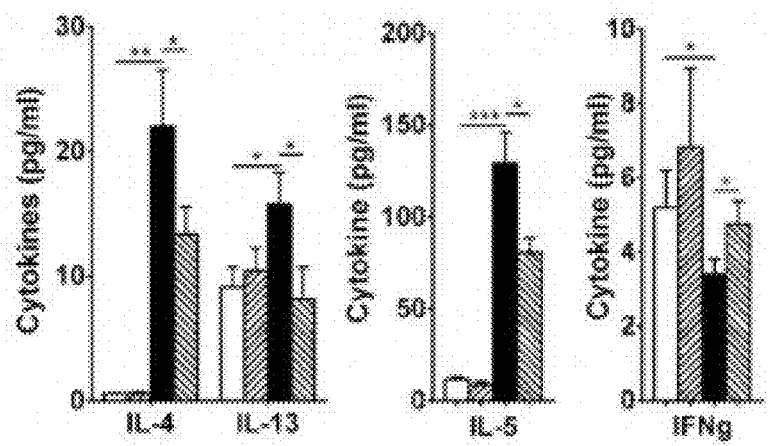
FIG. 5E, The Luminex Multiplex xMAP bead-based antibody assay was used to measure the concentrations of IFNγ, IL-4, IL-5 and IL-13 in BALF (n=6 mice/group; *, p<0.05; , p<0.01; *, p<0.001). Data are all shown as means±standard errors of the means (SEM).

Furthermore, RCM-1 decreased protein concentrations of IL-4, IL-5 and IL-13 in BALF (FIG. 5E) and IL-5 and IL-13 mRNAs in lung tissue (FIG. 5C). Similarly, Ccl2, Ccl11, Ccl24, Ccr2, Ccr3 and Acta2 mRNAs were inhibited by RCM-1 (FIG. 5C-D). RCM-1 increased IFNγ levels in BALF (FIG. 5E). There was no effect on IL-12p35, Cx3cl1, Ptgs2 or Ltc4s (FIG. 5C-D). Thus, RCM-1 decreased HDM-mediated inflammatory responses in the lung tissue but did not influence recruitment of inflammatory cells to BALF.

Figure 6A:
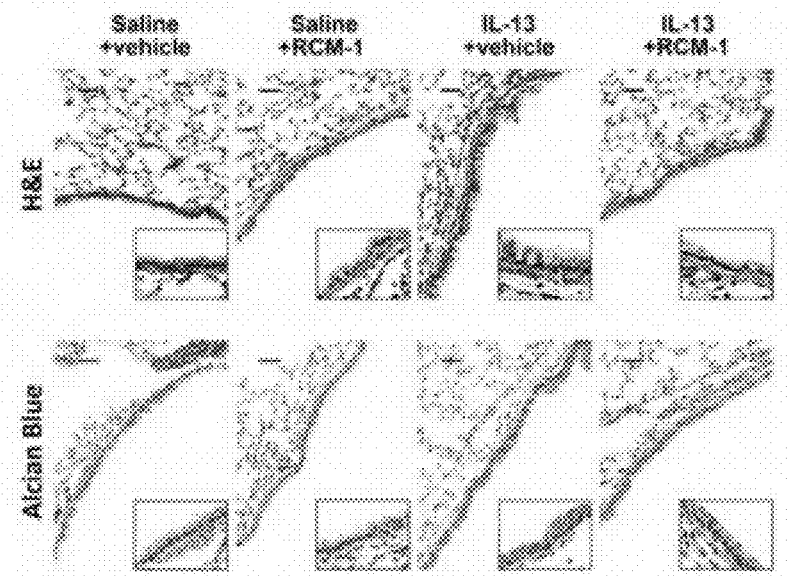
FIG. 6A-FIG. 6E. RCM-1 inhibits IL-13-induced goblet cell metaplasia.
Figure 6B:
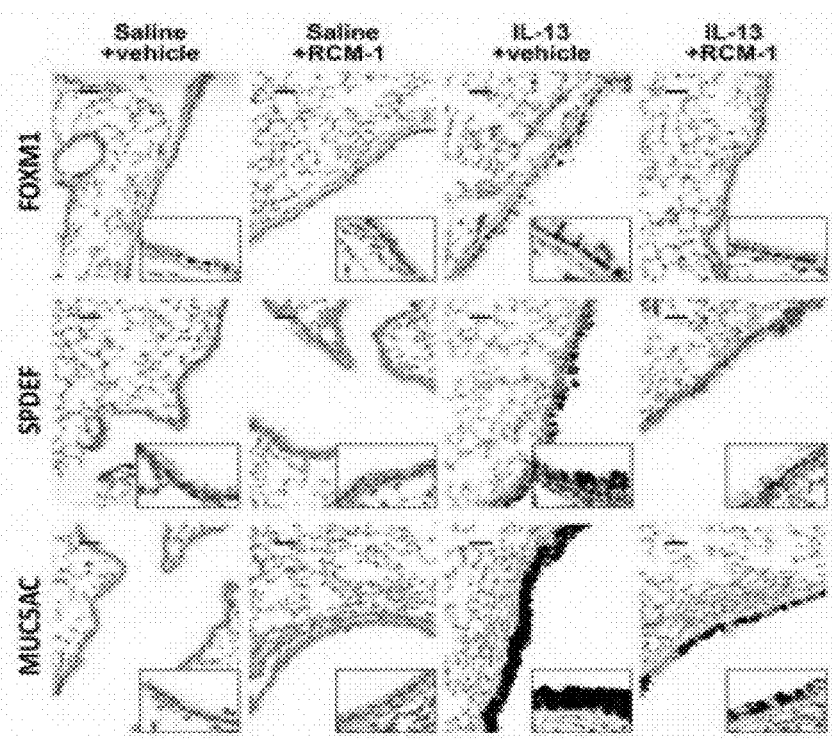
Figure 6C:
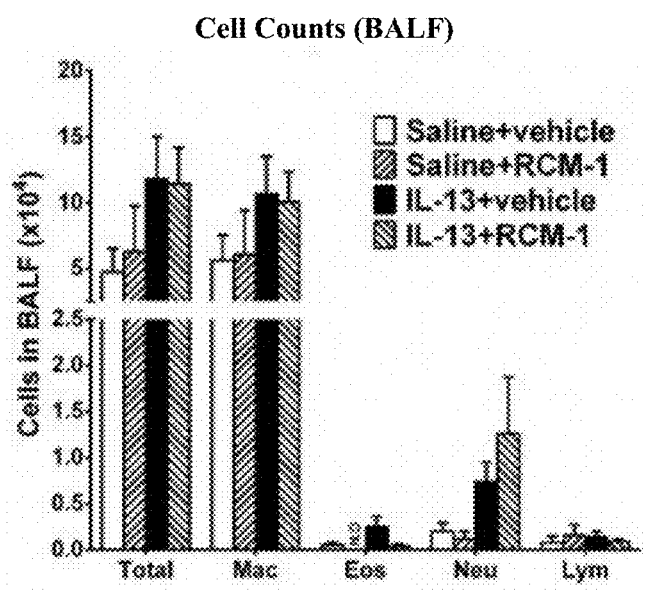
Figure 6D:
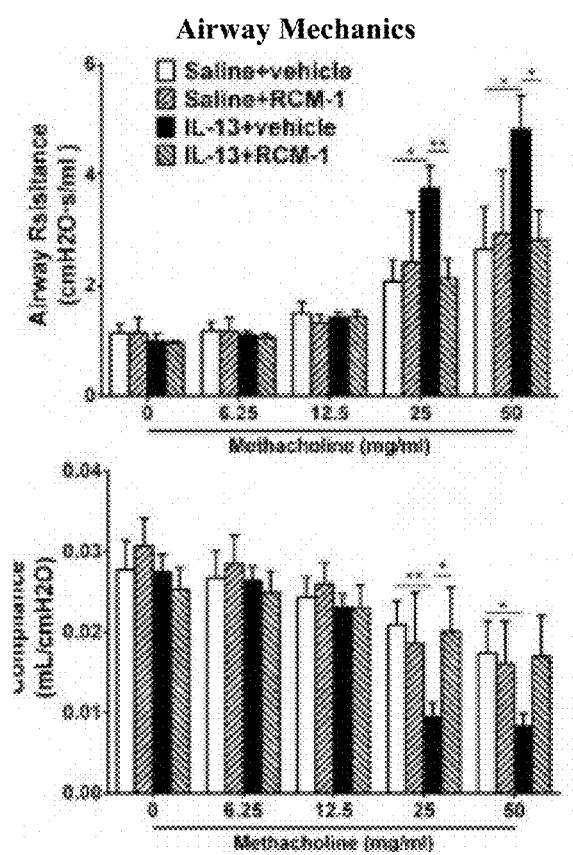
Figure 7A:
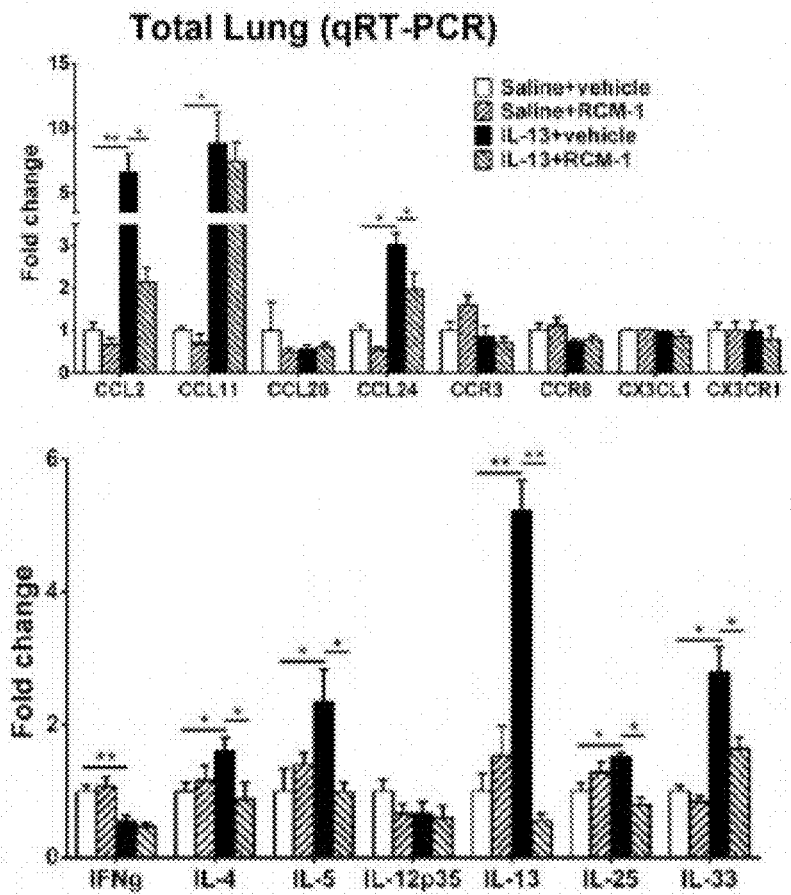
FIG. 7A-FIG. 7F. RCM-1 inhibits ERK1/2 but does not change phosphorylation of STAT6.
Figure 7B:
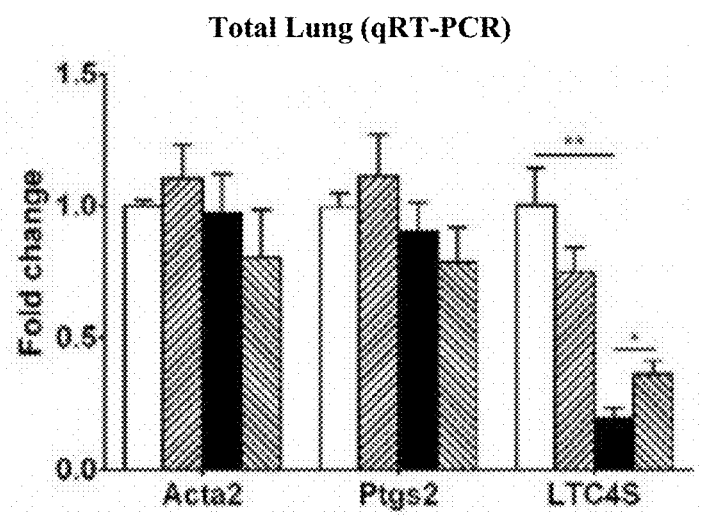
Figure 7C:
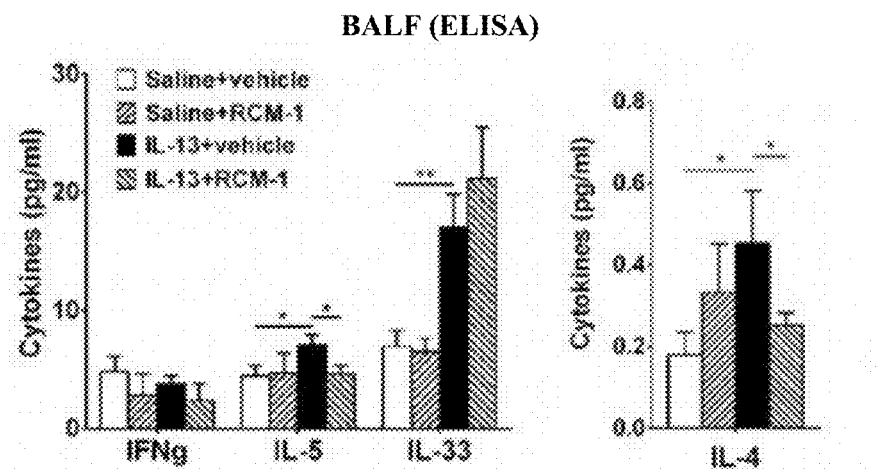
Figure 11A:
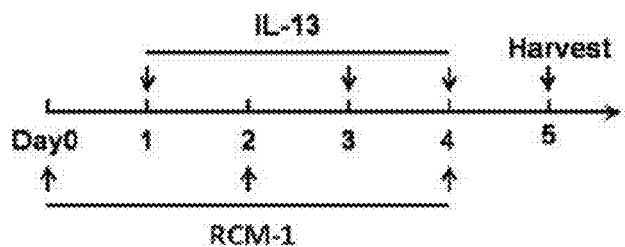
FIG. 11A-FIG. 11B. RCM-1 protects bronchiolar epithelial cells from IL-13-mediated inhibition of FOXA2.
Figure 11B:
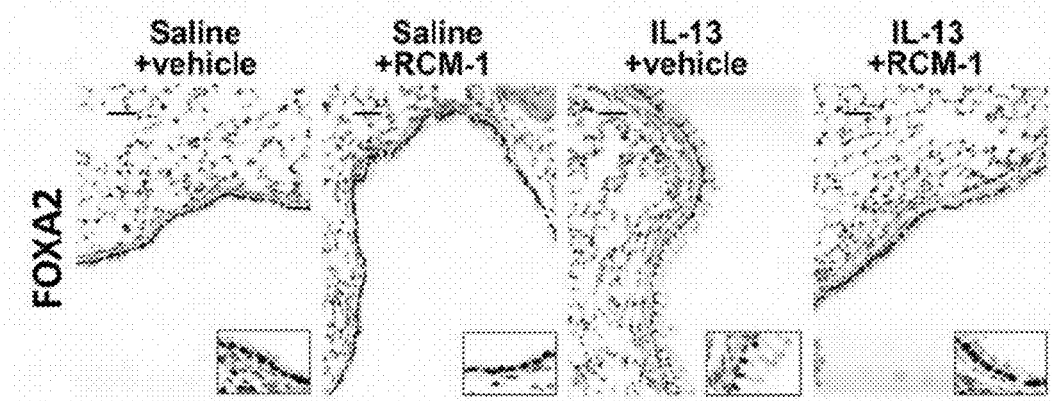
Figure 12:
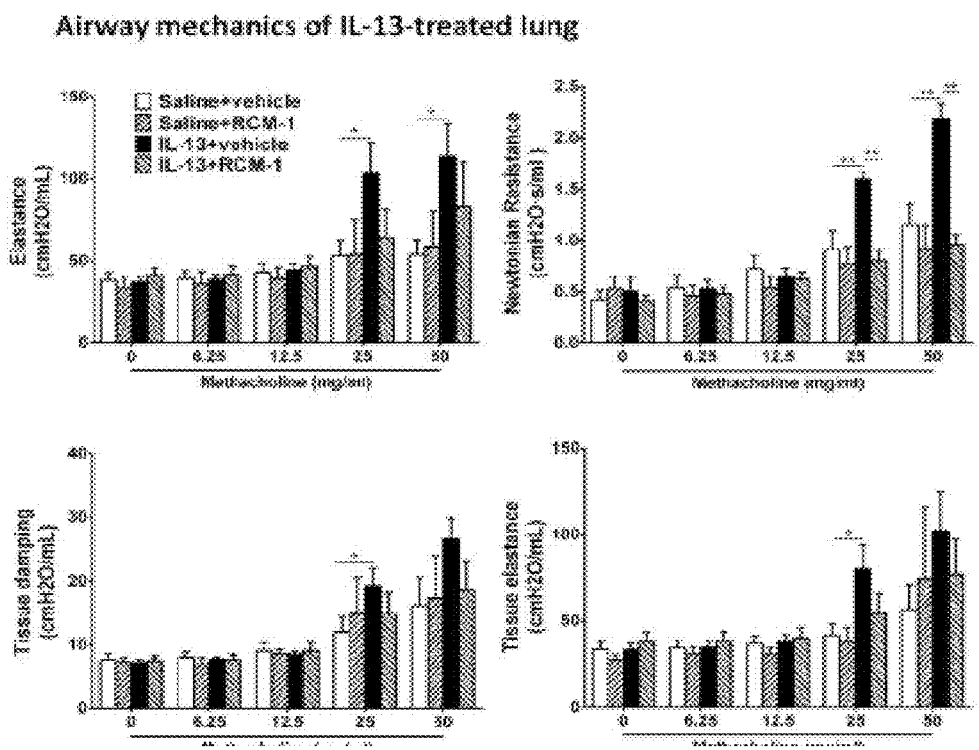
FIG. 12. Lung mechanics in mice treated with IL-13 and RCM-1. IL-13 was given to BALB/c mice by intranasal administration on days 1, 3 and 4. RCM-1 was given by i.p. injection on days 0, 2 and 4. FlexiVent was used to measure lung mechanics on day 5. IL-13 increased the Elastance, Newtonian resistance, Tissue damping and Tissue elastance. RCM-1 significantly reduced IL-13-mediated increase in Newtonian resistance (n=5 mice per group; *, P<0.05; **, P<0.01). Data are shown as means±standard errors of the means (SEM).
Figure 13:
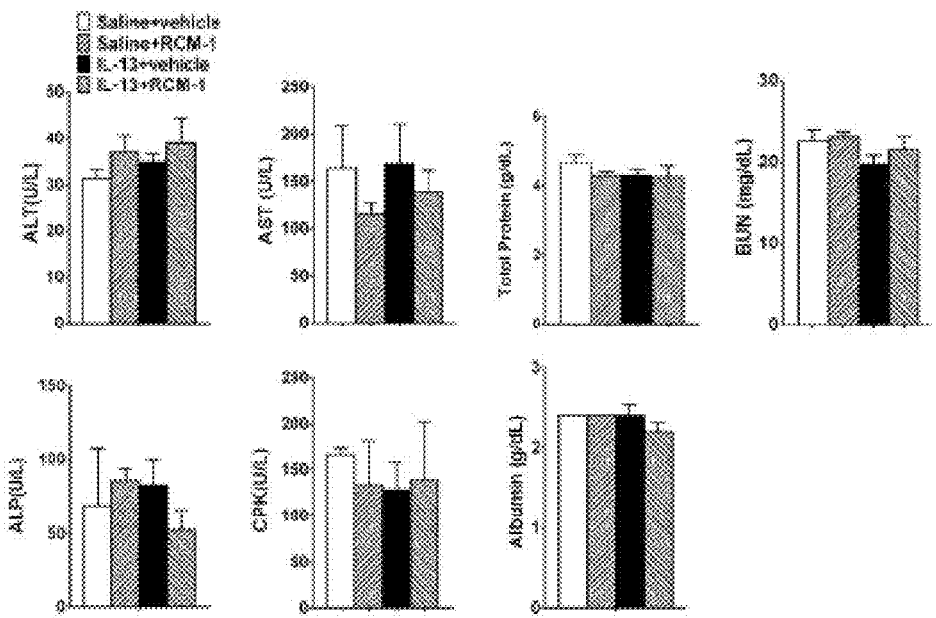
FIG. 13. Lack of toxicity of RCM-1 in IL-13-treated mice. IL-13 was given to BALB/c mice by intranasal administration on days 1, 3 and 4. RCM-1 was given by i.p. injection on days 0, 2 and 4. Serological analysis of blood serum was performed on day 5. RCM-1 did not affect the liver enzymes ALT and AST, blood urea nitrogen (BUN), creatine phosphokinase (CPK), alkaline phosphatase (ALP), albumin and total protein in blood serum (n=4 mice/group; *, P<0.05; **, P<0.01). Data are shown as means±standard errors of the means (SEM).

RCM-1 inhibits goblet cell metaplasia and airway hyperresponsiveness in response to IL-13. Published studies demonstrated that the IL-13/STAT6 signaling pathway induces goblet cell metaplasia (14). We tested whether RCM-1 influences IL-13/STAT6 signaling in vivo. Recombinant mouse IL-13 was administered intranasally to wild type BALB/c mice (FIG. 11A). RCM-1 decreased goblet cell metaplasia in IL-13-treated lungs as shown by Alcian blue staining (FIG. 6A) and immunostaining for MUC5AC, FOXM1 and SPDEF (FIG. 6B). In contrast, FOXA2 staining in airway epithelium was increased (11B). RCM-1 decreased airway resistance and improved lung function in IL-13-treated mice (FIGS. 6D and 12). Similar to HDM model, RCM-1 did not influence BALF cell counts (FIG. 6C), but reduced pro-inflammatory mediators in BALF and lung tissue (FIG. 7A-7sC). No toxicity was observed after RCM-1 treatment as assessed by serological analysis of blood serum (FIG. 13). Thus, RCM-1 reduced goblet cell metaplasia and improved lung function after IL-13 treatment.

Figure 6E:
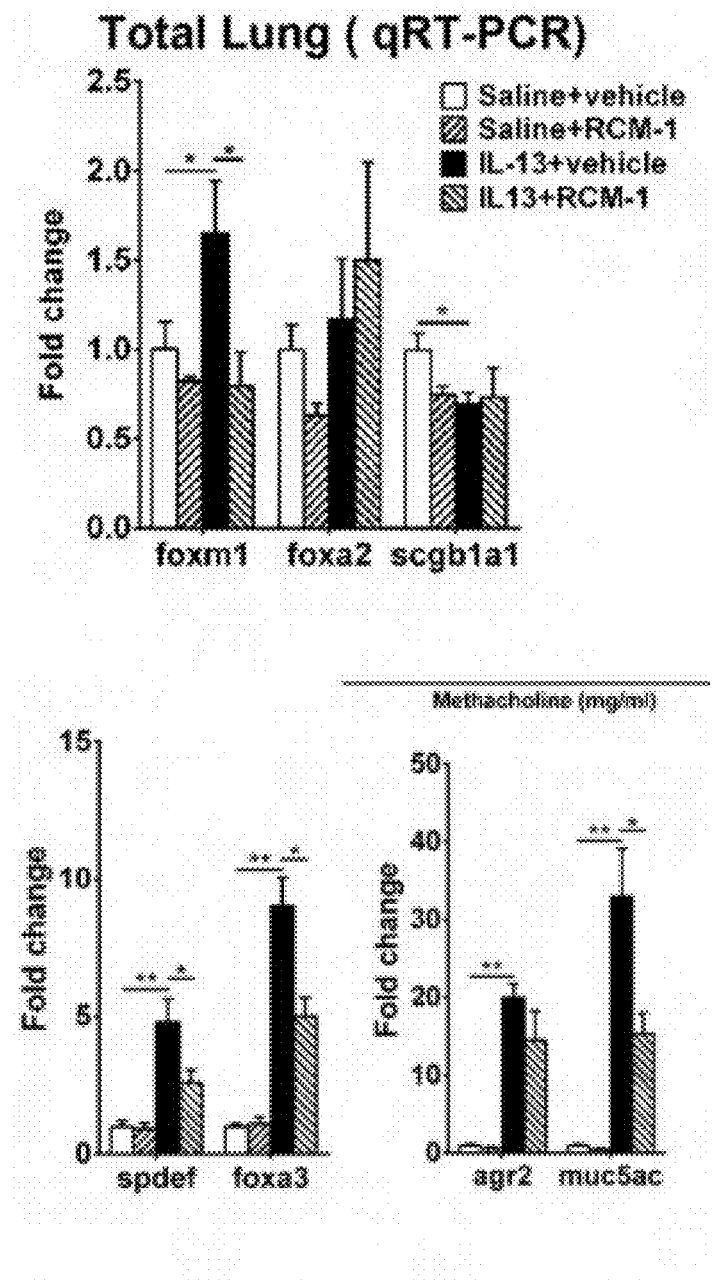
Figure 7D:
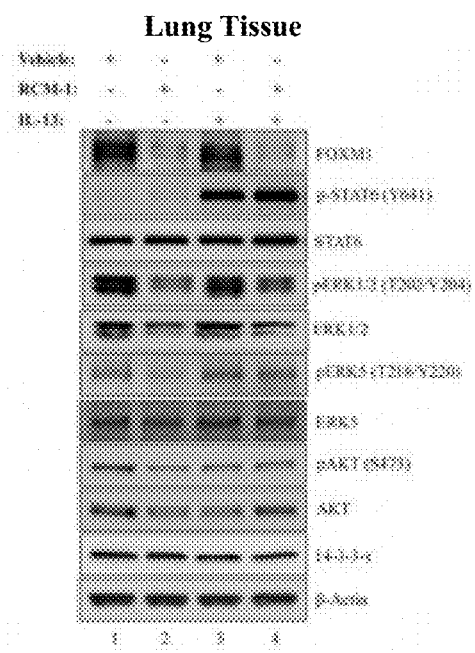
Figure 7E:
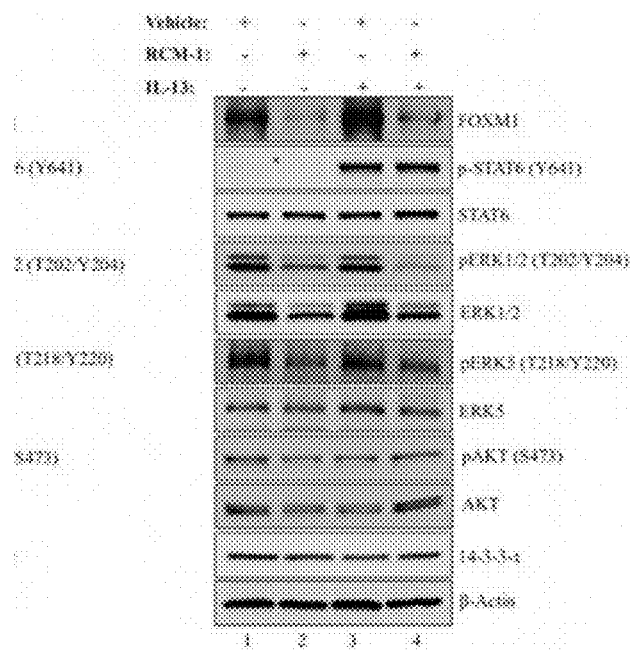
Figure 7F:
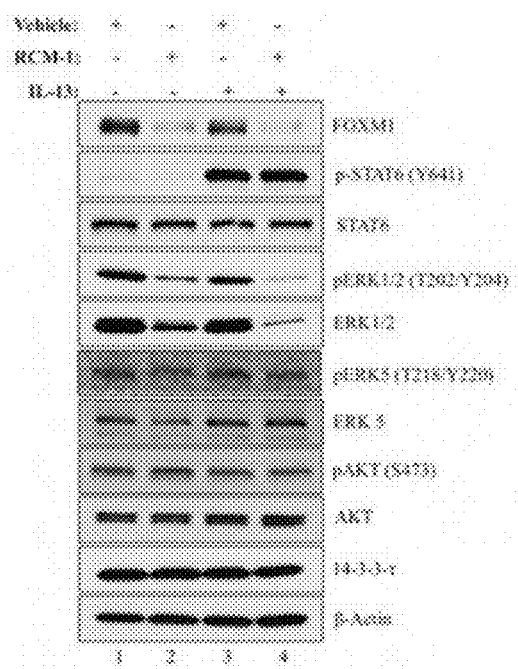
Figure 14:
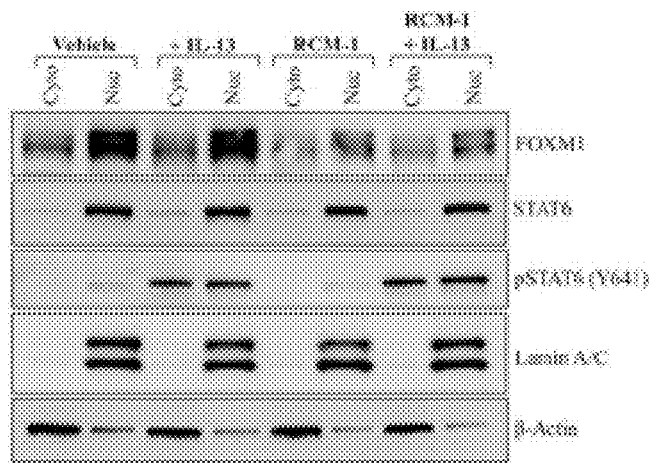
FIG. 14. RCM-1 inhibits nuclear accumulation of FOXM1 protein in A549 cells. Western blot was performed using cytoplasmic and nuclear extracts from A549 cells.

Since the IL-13/STAT6 and the MEK/ERK1/2 signaling pathways induce goblet cell metaplasia in airway epithelium (14, 21), we examined these pathways in RCM-1-treated lungs. RCM-1 effectively inhibited FOXM1 but did not change IL-13-induced phosphorylation of STAT6 in mouse lung tissue (FIG. 7D). RCM-1 had no effect on pSTAT6 in human airway epithelial cells (FIG. 7E) and lung adenocarcinoma A549 cells (FIG. 7F). Furthermore, nuclear amounts of pSTAT6 and total STAT6 were unaltered in RCM-1-treated cells (FIG. 14), indicating that RCM-1 does not affect nuclear translocation of pSTAT6 after IL-13 exposure. In contrast, nuclear amounts of FOXM1 were decreased (FIG. 14), a finding consistent with the initial discovery of RCM-1 as FOXM1 inhibitor (FIG. 1). Although RCM-1 had no effect on phosphorylation and nuclear translocation of STAT6, expression of IL-13/STAT6 downstream target genes Agr2, Muc5ac, Spdef and Foxa3 was reduced (FIG. 6E), suggesting that RCM-1 acts downstream of pSTAT6 to inhibit IL-13/STAT6 signaling in airway epithelium.

The RCM-1 compound inhibited pERK1/2 and total ERK1/2 in both IL-13-treated and control lungs (FIG. 7D). Furthermore, RCM-1 decreased pERK1/2 and total ERK1/2 in human airway epithelial cells and A549 cells and this effect was independent of IL-13 (FIG. 7E-F). RCM-1 did not alter AKT, pAKT, ERK5 and 14-3-3 protein in mouse lung tissue and in vitro (FIG. 7D-7F). Altogether, RCM-1 inhibited FOXM1, reduced ERK1/2 and decreased goblet cell metaplasia after IL-13 treatment.

Discussion

Previous studies demonstrated that FOXM1 is induced in airway epithelial cells and inflammatory cells of severe asthmatics and mice treated with ovalbumin (OVA) or house dust mite extract (HDM) (16). FOXM1 is an important regulator of embryonic development, carcinogenesis and organ regeneration, and its levels are aberrantly induced during chronic lung diseases (22-27). While FOXM1 is a positive regulator of cellular proliferation (18), it is also expressed in subsets of quiescent (non-cycling) cells (16, 28, 29) and its role in goblet cell differentiation is independent of cell cycle regulation (16). Conditional deletion of the Foxm1 gene from bronchiolar progenitor cells or inactivation of the FOXM1 protein by the membrane-penetrating ARF peptide inhibited expression of goblet cell-specific genes and protected mice from HDM-mediated allergic responses (16). These studies strongly support the concept that FOXM1 represents a potential therapeutic target to suppress mucus hyperplasia and lung inflammation.

Our previous studies have demonstrated that the ARF peptide, a synthetic inhibitor of FOXM1, binds to and sequesters FOXM1 in the nuclei, thereby inhibiting FOXM1 transcriptional activity (16, 17). While the ARF peptide is a specific and effective inhibitor of FOXM1, its clinical applications for treatment of chronic airway diseases are limited by the potential for immune response against the peptide. Several pharmacological agents inhibiting FOXM1 were previously identified, including thiazole antibiotics siomycin A and thiostrepton (30-32), and the FDI-6 small molecule compound (33). Siomycin A and thiostrepton are known proteasome inhibitors (34), and therefore, these compounds target multiple signaling pathways in addition to FOXM1. FDI-6 inhibits binding of FOXM1 to its target DNA (33). Since FOXM1 and other Forkhead (FOX) proteins share DNA-binding motifs, it is likely that the inhibition of Forkhead domain binding to DNA will influence other FOX transcription factors expressed in the lung, for example FOXA2, FOXJ1 and FOXF1, leading to off-target effects. In the present study, we developed a novel strategy for targeting the FOXM1 protein through inhibition of its nuclear localization. Decreased nuclear localization of FOXM1 caused rapid degradation of the FOXM1 protein in cultured airway epithelial cells and in vivo, inhibiting activation of FOXM1 target genes. Since FOXM1 regulates its own promoter via a positive feedback mechanism (34, 35), reduced Foxm1 mRNA observed in RCM-1-treated mice can be a consequence of inhibition of the FOXM1 protein by the RCM-1 compound. Interestingly, diminished nuclear localization of FOXM1 in RCM-1-treated lungs can be a result of decreased MEK/ERK1/2 signaling because ERK1/2 directly phosphorylates the FOXM1 protein and this phosphorylation is required for FOXM1 nuclear localization and its transcriptional activity (36). FOXM1 was shown to be required for KRAS/MEK/ERK1/2 signaling because genetic deletion of Foxm1 from respiratory epithelial cells reduced developmental defects and prevented lung carcinogenesis in mice expressing the activated form of KRAS (KrasG12D) (37, 38). The lack of observed toxicity and excellent biological responses in vivo, support the concept that RCM-1 or molecules sharing its structure and function are potentially useful agents for development of treatments for lung cancers with activating KRAS mutations as well as pulmonary disorders associated with mucus hyperproduction and inflammation.

RCM-1 prevented goblet cell metaplasia in response to HDM and recombinant IL-13. Since FOXM1 promotes differentiation of goblet cells from airway epithelial precursors, biological effects of RCM-1 are likely related to the direct inhibition of goblet cell differentiation. The observation that pSTAT6 levels were not affected by RCM-1 indicates that RCM-1 acts downstream of IL-13-mediated phosphorylation of STAT6. Findings that RCM-1 reduced expression of pSTAT6 target genes, such as arg2, foxa3, and muc5ac, are consistent with inhibitory effects of RCM-1 on pSTAT6 transcriptional activities. Since FOXM1 transcriptionally activates SPDEF (16), a master-regulator of goblet cell fate (14, 15), it is likely that effects of RCM-1 are mediated by its influence on the FOXM1-SPDEF regulatory cascade, to inhibit goblet cell differentiation. Interestingly, FOXM1 is expressed at the early stage of goblet cell differentiation and its expression is decreased in fully differentiated goblet cells (16). Based on the FOXM1 expression pattern in asthmatic airways, RCM-1 can be effective in preventing goblet cell metaplasia between acute exacerbations of asthma.

The RCM-1 compound inhibited ERK1/2 in cultured epithelial cells and in vivo. The MEK/ERK1/2 signaling pathway induces goblet cell metaplasia and allergen-mediated pulmonary inflammation (21, 39). The MEK inhibitor U0126 diminished ovalbumin-induced lung inflammation (39). Therefore, it is likely that a simultaneous inhibition of FOXM1 and ERK1/2 accounts for biological effects of RCM-1 in mouse asthma models. RCM-1 decreased airway resistance and increased compliance, findings consistent with reduced tissue stiffness and decreased inflammation. While numbers of T cells in BALF were not changed after RCM-1 treatment, expression of IL-4, IL-5, and IL-13 were reduced in BALF and lung. One explanation of this discrepancy is that RCM-1 may affect the activation status of T cells. Consistent with this hypothesis, FOXM1-deficient myeloid dendritic cells exhibited reduced antigen uptake and decreased expression of co-stimulatory molecules in co-culture experiments with T cells (16). Inhibition of ERK1 can also contribute to impaired Th2 responses in RCM-1-treated mice because genetic inactivation of ERK1 decreased Th2 differentiation and reduced allergic inflammation (40). Alternatively, RCM-1 may directly inhibit the production of IL-4, IL-5 and IL-13 by activated T cells because T-cell-specific deletion of Foxm1 disrupted maturation of T cells in vivo (29). Finally, it is also possible that the concentration and/or duration of RCM-1 treatment used in our studies are insufficient to fully inhibit allergen-mediated pulmonary inflammation.

In summary, we identified a novel FOXM1-inhibiting small molecule compound, RCM-1, which effectively prevented goblet cell metaplasia, decreased airway resistance and reduced lung inflammation in response to HDM and recombinant IL-13. Results of our studies may lead to clinical trials with FOXM1 inhibitors in patients with asthma and other chronic airway disorders.

Materials and Methods

The RCM-1 compound (2-{[2-oxo-2-(thiophen-2-yl)ethyl]sulfanyl}-4,6-di(thiophen-2-yl)pyridine-3-carbonitrile; empirical formula, C20H12N2OS4; molecular weight, 424.5874) can be obtained from Vitas-M Laboratory (catalog #STK747537).

Mouse strains and treatment with RCM-1. Mouse strains. BALB/c mice were purchased from Charles River Laboratories. Mice were 8 to 10 weeks old at the beginning of experiments. Generation of transgenic CCSP-rtTAtg/−/tetO-FOXM1tg/− (GFP-FOXM1-TG) mice and Doxycycline (Dox) treatments have been described previously (51). Animal studies were approved by the Animal Care and Use Committee of Cincinnati Children's Research Foundation.

The generation of transgenic CCSP-rtTAtg/−/tetO-Foxm1tg/− (GFP-FOXM1) mice has been previously described (19). Mice were given doxycycline (Dox) in food chow (625 mg/kg; Harlan Teklad, Madison, Wis.) to induce GFP-FOXM1 transgene. 8-10 weeks old BALB/c mice were purchased from Charles River Laboratories. The RCM-1 compound (2-{[2-oxo-2-(thiophen-2-yl)ethyl]sulfanyl}-4,6-di(thiophen-2-yl)pyridine-3-carbonitrile) was synthesized by Vitas-M Laboratory (the purity is 95%). RCM-1 was given to mice intraperitoneally (i.p.) (2 mg per kilogram of body weight). After injections, RCM-1 compound was detectable in blood serum and BALF using HPLC. HDM extract (100 µg, Greer Laboratories) and recombinant murine IL-13 (0.5 µg, Biolegend) were diluted in saline and given by intranasal administration. FlexiVent system was used to measure airway mechanics as described (41, 42). Animal studies were approved by the Animal Care and Use Committee of Cincinnati Children's Research Foundation.

Small molecule screen for FOXM1 inhibitors. Generation of U2OS C3 cells containing Dox-inducible GFP-FOXM1 fusion protein was previously described (17). For the small molecule screen, 2000 cells were plated per each well. Sixteen hours later, Dox (1 μg/ml) was added to the cell culture. After 24 hr, 50,000 small molecule compounds (4 μg/ml diluted in 0.1% of DMSO) from the chemical library of the Genome Research Institute at the University of Cincinnati were added in Dox-containing media. Cells were fixed 24 hr later and scanned for GFP using scanning PerkinElmer Opera imaging system.

qRT-PCR, Western blot and measurements of cytokines in BALF. RNA was prepared from whole lung tissue. A StepOnePlus real-time PCR system (Applied Biosystems, Foster City, Calif.) was used as described previously (37, 43). Samples were amplified with TaqMan gene expression mastermix (Applied Biosystems) combined with inventoried TaqMan gene expression assays for the gene of interest (Table 1). Reactions were analyzed in triplicate. Expression levels were normalized to β-actin mRNA. BALF concentrations of IL-4, IL-5, IL-13, IFNγ and IL-33 were measured by the Luminex Multiplex xMAP bead-based antibody assay according to manufacturer recommendations. Western blot analysis was performed as described previously (44-46) using either total lung protein or protein extract from human airway epithelial cells (Lonza) or A549 cells (ATCC). The antibodies and the air-liquid interface cell culture conditions are described in supplemental materials.

TABLE 1

TaqMan assays for qRT-PCR.

| Gene in TaqMan expression assay | Catalog no. |
|---|---|
| Human foxmI | Hs00153543_m1 |
| Mouse foxmI | Mm01184444_g1 |

TABLE 1-continued

TaqMan assays for qRT-PCR.

| Gene in TaqMan expression assay | Catalog no. |
|---|---|
| beta-actin | Mm00607939_s1 |
| acta2 | Mm00725412_s1 |
| agr2 | Mm01291804_m1 |
| ccl2 | Mm00441242_m1 |
| ccl11 | Mm00441238_m1 |
| ccl20 | Mm01268754_m1 |
| ccl24 | Mm00444701_m1 |
| ccr2 | Mm00438270_m1 |
| ccr3 | Mm00515543_g1 |
| ccr6 | Mm99999114_s1 |
| cx3cl1 | Mm00436454_m1 |
| cx3crI | Mm02620111_s1 |
| foxa2 | Mm01976556_s1 |
| foxa3 | Mm00484714_m1 |
| ifn-gama | Mm01168134_m1 |
| il-4 | Mm00445260_m1 |
| il-5 | Mm00439646_m1 |
| il-12p35 | Mm00434165_m1 |
| il-13 | Mm00434204_m1 |
| il-25 | Mm00499822_m1 |
| il-33 | Mm00505403_m1 |
| ltc4s | Mm00521864_m1 |
| muc5ac | Mm01276718_m1 |
| ptgs2 | Mm00478374_m1 |
| scgb1a1 | Mm00442046_m1 |
| spdef | Mm00600221_m1 |

Immunohistochemical staining. Lungs were inflated and used for preparation of either frozen or paraffin blocks. Five-μm sections were stained with hematoxylin and eosin (H&E), alcian blue or used for immunohistochemistry as described previously (37, 43, 47). Antibody-antigen complexes were detected using biotinylated secondary antibody followed by avidin-biotin-horseradish peroxidase complex (ABC), and 3,3'-diaminobenzidine (DAB) substrate (all from Vector Lab) (48, 49). Sections were counterstained with nuclear fast red. Immuno-fluorescent staining was performed as described in ((38, 50) and supplemental materials). Histological assessment and scoring were done in the pathology lab using criteria described in Table 2.

TABLE 2

Histological evaluation and scores.

| Histological Variable | Grade 0 | Grade 1 | Grade 2 | Grade 3 |
|---|---|---|---|---|
| Degree of inflammatory cell infiltration | Occasional mononuclear cells in the airway adventitia | Moderate cellular infiltration (lymphocytic, eosinophilic) of the bronchiolar adventitia with no or little infiltration of lamina propria | As in grade 1 but with increased cellular density and twofold thickness of the adventitia; mild epithelial infiltration; infiltrate lymphocytic, eosinophilic, or polymorphonuclear | Massive infiltration of either eosinophils or lymphocytes with increased polymorphonuclear cells at the periphery of the airway as well as adjacent blood vessels, between the smooth muscle fibers, within the lamina propria and epithelium |
| Vascular thickening/perivascular infiltrate | Normal intrapulmonary muscular arteries and pulmonary arteriole; no perivascular infiltrate | No changes to vascular wall but moderate perivascular infiltration of inflammatory cells | Hypertrophy of the media of muscular pulmonary arteries; moderate perivascular infiltration | As in grade 2 plus the proliferation of intimal cells and subendothelial fibrosis |
| Goblet cell metaplasia | Absent in terminal bronchioles; <10% of the epithelial cells within the bronchioles | <5% in the terminal bronchioles, <20% in the bronchioles and small bronchi | >10% goblet cells in the terminal bronchioles with >20% goblet cells in the bronchioles | >20% goblet cells in the terminal bronchioles and bronchioles |

TABLE 2-continued

Histological evaluation and scores.

| Histological Variable | Grade 0 | Grade 1 | Grade 2 | Grade 3 |
|---|---|---|---|---|
| Alveolar septa thickening | Alveolar epithelium consisting of 1 thin layer | Increased cellular density of alveolar septum | Infiltration by inflammatory cells | Inflammatory cell infiltration and increased connective tissue deposition |
| Smooth muscle hypertrophy or hyperplasia | Bronchioles 1-2 discontinuous layers | Bronchioles 2-3 discontinuous layers | Bronchioles 3-4 discontinuous layers | Bronchioles >4 layers and dense |
| Peribronchiolar fibrosis | Loose connective tissue composing the adventitia | Increased fiber density without increase in adventitial thickness | Well-formed fibrous tissue accompanied by inflammatory cell infiltration; little involvement of lamina propria | Lamina propria and adventitia replaced by connective tissue and 2normal thickness |

TABLE 3

| Group | Mouse No. | Degree of inflammatory/cell infiltration | Vascular thickening perivascular infiltration | Goblet cell metaplasia | Alveolar septa thickening | Smooth muscle hypertrophy/hyperplasia | Peribronchiolar fibrosis | Combined scores |
|---|---|---|---|---|---|---|---|---|
| Saline + vehicle | 1 | 1 | 0 | 0 | 0 | 0 | 0 | 1 |
| e | 2 | 0 | 0 | 0 | 0 | 0 | 0 | 0 |
|   | 3 | 0 | 0 | 0 | 0 | 0 | 0 | 0 |
| Saline + RCM-1 | 4 | 0 | 0 | 0 | 0 | 0 | 0 | 0 |
|   | 5 | 0 | 0 | 0 | 0 | 0 | 0 | 0 |
|   | 6 | 0 | 0 | 0 | 0 | 0 | 0 | 0 |
| HDM + vehicle | 7 | 3 | 3 | 2 | 2 | 1 | 1 | 12 |
|   | 8 | 3 | 3 | 1 | 1 | 1 | 0 | 9 |
|   | 9 | 2 | 2 | 1 | 1 | 1 | 1 | 8 |
| HDM + RCM-1 | 10 | 1 | 1 | 0 | 0 | 0 | 0 | 2 |
|   | 11 | 1 | 1 | 0 | 0 | 0 | 0 | 2 |
|   | 12 | 1 | 1 | 0 | 0 | 0 | 0 | 2 |

Asthma models and treatment with RCM-1. Three mouse models were used in this study. For GFP-FOXM1 transgenic mice, 100 μg of HDM extract (Greer Laboratories) was diluted in 100 μl of saline and given by intra-nasal administration on days 0 and 14. The RCM-1 compound (2-{[2-oxo-2-(thiophen-2-yl)ethyl]sulfanyl}-4,6-di(thiophen-2-yl)pyridine-3-carbonitrile; empirical formula, $C_{20}H_{12}N_2OS_4$; molecular weight, 424.5874) was synthesized by Vitas-M Laboratory. RCM-1 was administered intra-peritoneally (i.p.) (42.5 μg in 50 μl vehicle containing 25% DMSO, 25% ethanol and 50% corn oil) on days 12, 13 and 14. To induce GFP-FOXM1 transgene, mice were given Dox in food chow (625 mg/kg; Harlan Teklad, Madison, Wis.) from days 12 to 15. Dox-treated CCSP-rtTAtg/− littermates lacking the tetO-FOXM1 transgene were used as controls for GFP-FOXM1 TG mice. Twenty-four hours after the last HDM challenge, lungs were harvested for preparation of frozen sections and total protein.

In HDM-induced asthma model, BALB/c mice were given 100 μg of HDM (in 100 μl of sa-line) intra-nasally on days 0 and 14. RCM-1 or vehicle was given by i.p. injection on days 13, 15 and 16. 72 hours after the last HDM challenge, lungs were harvested for paraffin embedding as well as preparation of RNA and protein. FlexiVent small animal ventilator was used to measure airway mechanics as described (52-54).

For IL-13 treatment, 0.5 μg of carrier-free recombinant murine IL-13 (catlog No. 575902, Bio-legend) in 100 μl saline was given intra-nasally to BALB/c mice on days 1, 3 and 4. RCM-1 or ve-hide was given by i.p. injection on days 0, 2 and 4. On day 5, lungs were harvested for paraffin embedding and preparation of RNA and protein. For measurements of airway mechanics, mice were treated with 4 μg of IL-13 on days 1, 3 and 4, and 24 hr later the lung function was assessed on tracheostomized mice using a computerized FlexiVent system (SCIREQ, Montreal, Canada). Methacholine was delivered using an Aeroneb nebulizer (SCIREQ). Serological testing of blood serum was performed in the animal facility of Cincinnati Children's Research Foundation.

Cell culture of human bronchial epithelial cells. Primary human bronchial epithelial cells were purchased from Lonza (Walkersville, Md.) as cryopreserved passage 1 of normal human bronchial epithelium (NHBE, CC-25405, Lonza). Primary cultures were grown in B-ALI™ growth basal medium supplemented with BPE, Insulin, Hydrocortisone, GA-1000, Retinoic Acid, Transferrin, Triiodothyronine, Epinephrine, hEGF (all from B-ALI™ SingleQuots™ kit, Lonza) and Anti-Anti (containing 100 units/mL of penicillin, 100 μg/mL of streptomycin, and 0.25 μg/mL of Fungi-Zone® Antimycotic, Gibco® Life Technology). Cells were passaged using trypsin (CC-5034, Lonza) and used at passage 2-3.

For air-liquid interface cultures, NHBE cells were grown to confluence, harvested, and seed-ed at 5×10⁴ cells per insert on semi-permeable Transwell membranes (Transwell, 0.4 μm pore-size, 12 mm diameter; Corning Inc. Cambridge, Mass.) coated with 0.03 mg/ml collagen (BD Biosciences. Bedford, Mass.). Cells were grown submerged in growth basal medium. After 2 days, cells were ex-posed to air, and B-ALI™ differentiation medium was added to the basal chamber. Differentiation medium was supplemented with BPE, Insulin, Hydrocortisone, GA-1000, Retinoic Acid, Transfer-rin, Triiodothyronine, Epinephrine, hEGF (all from B-ALI™ SingleQuots™ kit, Lonza). All cultures were maintained at 37° C. in a humidified atmosphere of 5% CO2. One hour after RCM-1 treatment (1 μM), cells were treated with recombinant human IL-13 (10 ng/ml, eBioscience Inc.) and harvested two hours later.

Quantitative real-time RT-PCR (qRT-PCR). RNA was prepared from whole lung tissue. A StepOnePlus real-time PCR system (Applied Biosystems, Foster City, Calif.) was used as described previously (55, 56). Samples were amplified with TaqMan gene expression mastermix (Applied Bio-systems) combined with inventoried TaqMan gene expression assays for the genes of interest (Table 1). Reactions were analyzed in triplicate. Expression levels were normalized to β-actin mRNA.

Histological examination and immunohistochemistry. Lungs were inflated, fixed in 4% para-formaldehyde (PFA), and embedded into paraffin blocks. For frozen sections, lungs were inflated, fixed in 4% PFA for 24 hours and transferred to 30% sucrose/PBS solution followed by OCT treatment. Five-μm lung sections were stained with hematoxylin and eosin (H&E) or Alcian blue or used for immunohistochemistry as described previously (52, 55-57). The following antibodies were used for immunostaining: FOXM1 (1:500, C-20 and H-300, Santa Cruz Biotechnology), Clara cell-secreted protein (CCSP; 1:2,000, WRAB-CCSP; Seven Hill Bioreagents), FOXA2 (1:2,000, WRAB-FOXA2; Seven Hill Bioreagents); SPDEF (1:2,000; generated in the lab of J. A. Whitsett) (58) and MUC5AC (1:500, 45M1, ab3649; Abcam). Antibody-antigen complexes were detected using secondary antibody followed by the Avidin-biotin complex (ABC), and 3,3'-diaminobenzidine (DAB) substrate (all from Vector Lab). Sections were counterstained with nu-clear fast red (Vector Laboratories, Burlingame, Calif.). For co-localization experiments, slides were counterstained with DAPI (4',6'-diamidino-2-phenylindole; Vector Lab). Fluorescent images were obtained using a Zeiss Axioplan2 microscope equipped with an Axiocam MRm digital cam-era and Axiovision 4.3 software (Carl Zeiss Microimaging, Thornwood, N.Y.).

Histological assessment and scoring was performed in pathology core of Cincinnati Children's Hospital using H&E-stained sections. The assessment included inflammatory cell infiltration of the bronchiolar wall, goblet cell metaplasia, vascular thickening/perivascular infiltrate, smooth muscle hyperplasia, alveolar septa thickening and peribronchiolar fibrosis (Table 2).

Measurement of BALF cytokines and Western blot. The Luminex Multiplex xMAP bead-based antibody assay was used to measure the concentrations of IFNγ, IL-4, IL-5, IL-13 and IL-33 in BALF according to manufacturer's recommendations. For Western blot, protein extracts were pre-pared from NHBE cells or lung tissue using RIPA buffer. Western blot analysis was done as de-scribed previously (59, 60). Primary antibodies were incubated overnight at 4° C. in 5% nonfat, dry milk. β-Actin was used as loading control. The following antibodies were used for Western blot: FOXM1 (C-20), FACT140 (28734), NFkB-p65 (372), STAT6 (C-9) and β-actin (C-11) (all from Santa Cruz Biotechnology); YAP (4912S), phospho-STAT6 (9631), ERK1/2 (4695), pERK1/2 (4370), AKT (4687), pAKT (3787), ERK5 (3552) and pERK5 (3371) (all from Cell Signaling Technology); FOXA2 (WRAB-1200) and FOXJ1 (WMAB-319) (all from Seven Hills Biorea-gents, Cincinnati, Ohio). Other Abs were 14-3-3 (Bethyl Labs) and GFP (A11122, Life Technolo-gies). The signals from primary Abs were amplified by HRP-conjugated secondary Abs (Bio-Rad, Hercules, Calif.) and detected with Enhanced Chemiluminescence Plus (Amersham Pharmacia Bio-tech, Piscataway, N.J.) followed by autoradiography.

Statistical analysis. Student's t test and multivariant ANOVA was used to determine statistical significance. P values<0.05 were considered significant. Values were expressed as means±standard deviations (SD) or means±standard error (SE) as indicated in figure legends.

REFERENCES

1. C. Ober, T. C. Yao, The genetics of asthma and allergic disease: a 21st century perspective. Immunological reviews 242, 10-30 (2011).
2. G. W. Wong, M. Miravitlles, A. Chisholm, J. A. Krishnan, Respiratory guidelines—which real world? Annals of the American Thoracic Society 11 Suppl 2, S85-91 (2014).
3. C. A. Herrick, K. Bottomly, To respond or not to respond: T cells in allergic asthma. Nat Rev Immunol 3, 405-412 (2003).
4. S. A. Saenz, M. Noti, D. Artis, Innate immune cell populations function as initiators and effectors in Th2 cytokine responses. Trends in immunology 31, 407-413 (2010).
5. D. E. Smith, IL-33: a tissue derived cytokine pathway involved in allergic inflammation and asthma. Clin Exp Allergy 40, 200-208 (2010).
6. H. Hammad, B. N. Lambrecht, Barrier Epithelial Cells and the Control of Type 2 Immunity. Immunity 43, 29-40 (2015).
7. J. A. Krishnan, S. Q. Davis, E. T. Naureckas, P. Gibson, B. H. Rowe, An umbrella review: corticosteroid therapy for adults with acute asthma. The American journal of medicine 122, 977-991 (2009).
8. J. A. Whitsett, S. E. Wert, B. C. Trapnell, Genetic disorders influencing lung formation and function at birth. Hum Mol Genet 13 Spec No 2, R207-R215 (2004).
9. J. R. Rock, M. W. Onaitis, E. L. Rawlins, Y. Lu, C. P. Clark, Y. Xue, S. H. Randell, B. L. Hogan, Basal cells as stem cells of the mouse trachea and human airway epithelium. Proceedings of the National Academy of Sciences of the United States of America 106, 12771-12775 (2009).
10. J. R. Rock, X. Gao, Y. Xue, S. H. Randell, Y. Y. Kong, B. L. Hogan, Notch-dependent differentiation of adult airway basal stem cells. Cell stem cell 8, 639-648 (2011).
11. E. L. Rawlins, T. Okubo, Y. Xue, D. M. Brass, R. L. Auten, H. Hasegawa, F. Wang, B. L. Hogan, The role of Scgb1a1+ Clara cells in the long-term maintenance and repair of lung airway, but not alveolar, epithelium. Cell stem cell 4, 525-534 (2009).
12. T. Doherty, D. Broide, Cytokines and growth factors in airway remodeling in asthma. Current opinion in immunology 19, 676-680 (2007).
13. J. W. Tyner, E. Y. Kim, K. Ide, M. R. Pelletier, W. T. Roswit, J. D. Morton, J. T. Battaile, A. C. Patel, G. A. Patterson, M. Castro, M. S. Spoor, Y. You, S. L. Brody, M. J. Holtzman, Blocking airway mucous cell metaplasia by inhibiting EGFR antiapoptosis and IL-13 transdifferentiation signals. The Journal of clinical investigation 116, 309-321 (2006).
14. K. S. Park, T. R. Korfhagen, M. D. Bruno, J. A. Kitzmiller, H. Wan, S. E. Wert, G. K. Khurana Hershey, G. Chen, J. A. Whitsett, SPDEF regulates goblet cell hyperplasia in the airway epithelium. The Journal of clinical investigation 117, 978-988 (2007).

15. G. Chen, T. R. Korfhagen, Y. Xu, J. Kitzmiller, S. E. Wert, Y. Maeda, A. Gregorieff, H. Clevers, J. A. Whitsett, SPDEF is required for mouse pulmonary goblet cell differentiation and regulates a network of genes associated with mucus production. The Journal of clinical investigation 119, 2914-2924 (2009).
16. X. Ren, T. A. Shah, V. Ustiyan, Y. Zhang, J. Shinn, G. Chen, J. A. Whitsett, T. V. Kalin, V. V. Kalinichenko, FOXM1 promotes allergen-induced goblet cell metaplasia and pulmonary inflammation. Molecular and cellular biology 33, 371-386 (2013).
17. V. V. Kalinichenko, M. Major, X. Wang, V. Petrovic, J. Kuechle, H. M. Yoder, B. Shin, A. Datta, P. Raychaudhuri, R. H. Costa, Forkhead Box m1b Transcription Factor is Essential for Development of Hepatocellular Carcinomas and is Negatively Regulated by the p19ARF Tumor Suppressor. Genes & development 18, 830-850. (2004).
18. R. H. Costa, V. V. Kalinichenko, M. L. Major, P. Raychaudhuri, New and unexpected: forkhead meets ARF. Curr Opin Genet Dev 15, 42-48 (2005).
19. I. C. Wang, Y. Zhang, J. Snyder, M. J. Sutherland, M. S. Burhans, J. M. Shannon, H. J. Park, J. A. Whitsett, V. V. Kalinichenko, Increased expression of FoxM1 transcription factor in respiratory epithelium inhibits lung sacculation and causes Clara cell hyperplasia. Developmental biology 347, 301-314 (2010).
20. I. P. Lewkowich, S. Lajoie, J. R. Clark, N. S. Herman, A. A. Sproles, M. Wills-Karp, Allergen uptake, activation, and IL-23 production by pulmonary myeloid DCs drives airway hyperresponsiveness in asthma-susceptible mice. PloS one 3, e3879 (2008).
21. V. V. Polosukhin, J. M. Cates, W. E. Lawson, A. P. Milstone, A. G. Matafonov, P. P. Massion, J. W. Lee, S. H. Randell, T. S. Blackwell, Hypoxia-inducible factor-1 signalling promotes goblet cell hyperplasia in airway epithelium. J Pathol 224, 203-211 (2011).
22. W. Korver, M. W. Schilham, P. Moerer, M. J. van den Hoff, K. Dam, W. H. Lamers, R. H. Medema, H. Clevers, Uncoupling of S phase and mitosis in cardiomyocytes and hepatocytes lacking the winged-helix transcription factor trident. Curr Biol 8, 1327-1330 (1998).
23. K. Krupczak-Hollis, X. Wang, V. V. Kalinichenko, G. A. Gusarova, I.-C. Wang, M. B. Dennewitz, H. M. Yoder, H. Kiyokawa, K. H. Kaestner, R. H. Costa, The Mouse Forkhead Box m1 Transcription Factor is Essential for Hepatoblast Mitosis and Development of Intrahepatic Bile Ducts and Vessels during Liver Morphogenesis. Developmental biology 276, 74-88 (2004).
24. I. M. Kim, S. Ramakrishna, G. A. Gusarova, H. M. Yoder, R. H. Costa, V. V. Kalinichenko, The forkhead box M1 transcription factor is essential for embryonic development of pulmonary vasculature. The Journal of biological chemistry 280, 22278-22286 (2005).
25. M. K. Mirza, Y. Sun, Y. D. Zhao, H. H. Potula, R. S. Frey, S. M. Vogel, A. B. Malik, Y. Y. Zhao, FoxM1 regulates re-annealing of endothelial adherens junctions through transcriptional control of beta-catenin expression. The Journal of experimental medicine 207, 1675-1685 (2010).
26. Y. Liu, R. T. Sadikot, G. R. Adami, V. V. Kalinichenko, S. Pendyala, V. Natarajan, Y. Y. Zhao, A. B. Malik, FoxM1 mediates the progenitor function of type II epithelial cells in repairing alveolar injury induced by *Pseudomonas aeruginosa*. The Journal of experimental medicine 208, 1473-1484 (2011).
27. D. Balli, Y. Zhang, J. Snyder, V. V. Kalinichenko, T. V. Kalin, Endothelial Cell-Specific Deletion of Transcription Factor FoxM1 Increases Urethane-Induced Lung Carcinogenesis. Cancer research 71, 40-50 (2011).
28. T. V. Kalin, V. Ustiyan, V. V. Kalinichenko, Multiple faces of FoxM1 transcription factor: lessons from transgenic mouse models. Cell cycle (Georgetown, Tex. 10, 396-405 (2011).
29. L. Xue, L. Chiang, B. He, Y. Y. Zhao, A. Winoto, FoxM1, a forkhead transcription factor is a master cell cycle regulator for mouse mature T cells but not double positive thymocytes. PloS one 5, e9229 (2010).
30. S. K. Radhakrishnan, U. G. Bhat, D. E. Hughes, I. C. Wang, R. H. Costa, A. L. Gartel, Identification of a chemical inhibitor of the oncogenic transcription factor forkhead box M1. Cancer research 66, 9731-9735 (2006).
31. J. M. Kwok, S. S. Myatt, C. M. Marson, R. C. Coombes, D. Constantinidou, E. W. Lam, Thiostrepton selectively targets breast cancer cells through inhibition of forkhead box M1 expression. Molecular cancer therapeutics 7, 2022-2032 (2008).
32. N. S. Hegde, D. A. Sanders, R. Rodriguez, S. Balasubramanian, The transcription factor FOXM1 is a cellular target of the natural product thiostrepton. Nature chemistry 3, 725-731 (2011).
33. M. V. Gormally, T. S. Dexheimer, G. Marsico, D. A. Sanders, C. Lowe, D. Matak-Vinkovic, S. Michael, A. Jadhav, G. Rai, D. J. Maloney, A. Simeonov, S. Balasubramanian, Suppression of the FOXM1 transcriptional programme via novel small molecule inhibition. Nature communications 5, 5165 [Epub ahead of print] (2014).
34. M. Halasi, A. L. Gartel, Targeting FOXM1 in cancer. Biochemical pharmacology 85, 644-652 (2013).
35. X. H. Cheng, M. Black, V. Ustiyan, T. Le, L. Fulford, A. Sridharan, M. Medvedovic, V. V. Kalinichenko, J. A. Whitsett, T. V. Kalin, SPDEF inhibits prostate carcinogenesis by disrupting a positive feedback loop in regulation of the Foxm1 oncogene. PLoS genetics 10, e1004656 (2014).
36. R. Y. Ma, T. H. Tong, A. M. Cheung, A. C. Tsang, W. Y. Leung, K. M. Yao, Raf/MEK/MAPK signaling stimulates the nuclear translocation and transactivating activity of FOXM1c. Journal of cell science 118, 795-806. (2005).
37. I. C. Wang, J. Snyder, Y. Zhang, J. Lander, Y. Nakafuku, J. Lin, G. Chen, T. V. Kalin, J. A. Whitsett, V. V. Kalinichenko, Foxm1 Mediates Cross Talk between Kras/Mitogen-Activated Protein Kinase and Canonical Wnt Pathways during Development of Respiratory Epithelium. Molecular and cellular biology 32, 3838-3850 (2012).
38. I. C. Wang, V. Ustiyan, Y. Zhang, Y. Cai, T. V. Kalin, V. V. Kalinichenko, Foxm1 transcription factor is required for the initiation of lung tumorigenesis by oncogenic Kras(G12D.). Oncogene 33, 5391-5396 (2014).
39. W. Duan, J. H. Chan, C. H. Wong, B. P. Leung, W. S. Wong, Anti-inflammatory effects of mitogen-activated protein kinase kinase inhibitor U0126 in an asthma mouse model. J Immunol 172, 7053-7059 (2004).
40. N. Goplen, Z. Karim, L. Guo, Y. Zhuang, H. Huang, M. M. Gorska, E. Gelfand, G. Pages, J. Pouyssegur, R. Alam, ERK1 is important for Th2 differentiation and development of experimental asthma. FASEB J 26, 1934-1945 (2012).
41. V. Ustiyan, S. E. Wert, M. Ikegami, I. C. Wang, T. V. Kalin, J. A. Whitsett, V. V. Kalinichenko, Foxm1 transcription factor is critical for proliferation and differentiation of Clara cells during development of conducting airways. Developmental biology 370, 198-212 (2012).

42. T. V. Kalin, L. Meliton, A. Y. Meliton, X. Zhu, J. A. Whitsett, V. V. Kalinichenko, Pulmonary mastocytosis and enhanced lung inflammation in mice heterozygous null for the Foxf1 gene. American journal of respiratory cell and molecular biology 39, 390-399 (2008).
43. V. Ustiyan, I. C. Wang, X. Ren, Y. Zhang, J. Snyder, Y. Xu, S. E. Wert, J. L. Lessard, T. V. Kahn, V. V. Kalinichenko, Forkhead box M1 transcriptional factor is required for smooth muscle cells during embryonic development of blood vessels and esophagus. Developmental biology 336, 266-279 (2009).
44. D. Malin, I. M. Kim, E. Boetticher, T. V. Kalin, S. Ramakrishna, L. Meliton, V. Ustiyan, X. Zhu, V. V. Kalinichenko, Forkhead box F1 is essential for migration of mesenchymal cells and directly induces integrin-beta3 expression. Molecular and cellular biology 27, 2486-2498 (2007).
45. C. Bolte, X. Ren, T. Tomley, V. Ustiyan, A. Pradhan, A. Hoggatt, T. V. Kalin, B. P. Herring, V. V. Kalinichenko, Forkhead box F2 regulation of platelet-derived growth factor and myocardin/serum response factor signaling is essential for intestinal development. The Journal of biological chemistry 290, 7563-7575 (2015).
46. H. Xia, X. Ren, C. S. Bolte, V. Ustiyan, Y. Zhang, T. A. Shah, T. V. Kalin, J. A. Whitsett, V. V. Kalinichenko, Foxm1 regulates resolution of hyperoxic lung injury in newborns. American journal of respiratory cell and molecular biology 52, 611-621 (2015).
47. X. Ren, Y. Zhang, J. Snyder, E. R. Cross, T. A. Shah, T. V. Kahn, V. V. Kalinichenko, Forkhead box M1 transcription factor is required for macrophage recruitment during liver repair. Molecular and cellular biology 30, 5381-5393 (2010).
48. V. V. Kalinichenko, Y. Zhou, B. Shin, D. Beer-Stoltz, S. C. Watkins, W. J. A., R. H. Costa, Wild Type Levels of the Mouse Forkhead Box f1 Gene are Essential for Lung Repair. Am J Physiol Lung Cell Mol Physiol. 282, L1253-L1265 (2002).
49. I. M. Kim, Y. Zhou, S. Ramakrishna, D. E. Hughes, J. Solway, R. H. Costa, V. V. Kalinichenko, Functional characterization of evolutionary conserved DNA regions in forkhead box f1 gene locus. The Journal of biological chemistry 280, 37908-37916 (2005).
50. V. V. Kalinichenko, G. A. Gusarova, B. Shin, R. Costa, The Forkhead Box F1 Transcription Factor is Expressed in Brain and Head Mesenchyme during Mouse Embryonic Development. Gene Expression Patterns 3, 153-158 (2003).

SUPPLEMENTAL REFERENCES

51. I. C. Wang, Y. Zhang, J. Snyder, M. J. Sutherland, M. S. Burhans, J. M. Shannon, H. J. Park, J. A. Whitsett, V. V. Kalinichenko, Increased expression of FoxM1 transcription factor in respiratory epithelium inhibits lung sacculation and causes Clara cell hyperplasia. Developmental biology 347, 301-314 (2010).
52. X. Ren, T. A. Shah, V. Ustiyan, Y. Zhang, J. Shinn, G. Chen, J. A. Whitsett, T. V. Kalin, V. V. Kalinichenko, FOXM1 promotes allergen-induced goblet cell metaplasia and pulmonary inflammation. Molecular and cellular biology 33, 371-386 (2013).
53. V. Ustiyan, S. E. Wert, M. Ikegami, I. C. Wang, T. V. Kalin, J. A. Whitsett, V. V. Kalinichenko, Foxm1 transcription factor is critical for proliferation and differentiation of Clara cells during development of conducting airways. Developmental biology 370, 198-212 (2012).
54. T. V. Kalin, L. Meliton, A. Y. Meliton, X. Zhu, J. A. Whitsett, V. V. Kalinichenko, Pulmonary mastocytosis and enhanced lung inflammation in mice heterozygous null for the Foxf1 gene. American journal of respiratory cell and molecular biology 39, 390-399 (2008).
55. I. C. Wang, J. Snyder, Y. Zhang, J. Lander, Y. Nakafuku, J. Lin, G. Chen, T. V. Kalin, J. A. Whitsett, V. V. Kalinichenko, Foxm1 Mediates Cross Talk between Kras/Mitogen-Activated Protein Kinase and Canonical Wnt Pathways during Development of Respiratory Epithelium. Molecular and cellular biology 32, 3838-3850 (2012).
56. V. Ustiyan, I. C. Wang, X. Ren, Y. Zhang, J. Snyder, Y. Xu, S. E. Wert, J. L. Lessard, T. V. Kalin, V. V. Kalinichenko, Forkhead box M1 transcriptional factor is required for smooth muscle cells during embryonic development of blood vessels and esophagus. Developmental biology 336, 266-279 (2009).
57. X. Ren, Y. Zhang, J. Snyder, E. R. Cross, T. A. Shah, T. V. Kalin, V. V. Kalinichenko, Forkhead box M1 transcription factor is required for macrophage recruitment during liver repair. Molecular and cellular biology 30, 5381-5393 (2010).
58. G. Chen, T. R. Korfhagen, Y. Xu, J. Kitzmiller, S. E. Wert, Y. Maeda, A. Gregorieff, H. Clevers, J. A. Whitsett, SPDEF is required for mouse pulmonary goblet cell differentiation and regulates a network of genes associated with mucus production. The Journal of clinical investigation 119, 2914-2924 (2009).
59. D. Malin, I. M. Kim, E. Boetticher, T. V. Kalin, S. Ramakrishna, L. Meliton, V. Ustiyan, X. Zhu, V. V. Kalinichenko, Forkhead box F1 is essential for migration of mesenchymal cells and directly induces integrin-beta3 expression. Molecular and cellular biology 27, 2486-2498 (2007).
60. H. Xia, X. Ren, C. S. Bolte, V. Ustiyan, Y. Zhang, T. A. Shah, T. V. Kalin, J. A. Whitsett, V. V. Kalinichenko, Foxm1 regulates resolution of hyperoxic lung injury in newborns. American journal of respiratory cell and molecular biology 52, 611-621 (2015).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising

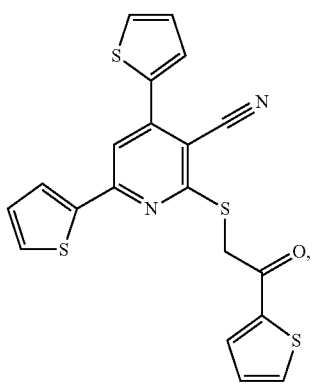

(Compound I)

or a pharmaceutically acceptable salt thereof; and a pharmaceutically acceptable excipient.

2. The composition of claim 1 for the treatment or amelioration of a symptom of an airway disorder.

3. The composition of claim 2, wherein said airway disorder is selected from asthma, chronic obstructive pulmonary disease (COPD), cystic fibrosis (CF), allergic disorders, pulmonary inflammatory diseases, pulmonary fibrosis, interstitial lung diseases, or a combination thereof.

4. The composition of claim 1, wherein said composition is administered in an amount sufficient to reduce one or more indices of airway dysfunction selected from inflammatory cell infiltration, vascular thickening/perivascular infiltration, goblet cell metaplasia, alveolar septa thickening, smooth muscle hypertrophy/hyperplasia, peribronchiolar fibrosis, lung tissue inflammation, airway hyperresponsiveness, mucus hyperplasia, decreased lung compliance, increased airway resistance, pro-inflammatory cytokine production, or a combination thereof.

5. The composition of claim 1, wherein said compound is present in an amount sufficient to inhibit FOXM1 in an individual upon administration of said composition to said individual.

6. The composition of claim 2, wherein said airway disorder is characterized by a condition selected from goblet cell metaplasia, lung tissue inflammation, increased airway hyperresponsiveness, mucus hyperplasia, decreased airway resistance, increased production of pro-inflammatory cytokines, or a combination thereof.

* * * * *